(12) United States Patent
Kutchan et al.

(10) Patent No.: US 7,390,642 B2
(45) Date of Patent: Jun. 24, 2008

(54) SALUTARIDINOL 7-O-ACETYLTRANSFERASE AND DERIVATIVES THEREOF

(75) Inventors: Toni M. Kutchan, Halle (DE); Meinhart H. Zenk, Halle (DE); Torsten Grothe, Kuerten (DE)

(73) Assignee: Donald Danforth Plant Science Center, St. Louis, MO (US)

( * ) Notice: Subject to any disclaimer, the term of this patent is extended or adjusted under 35 U.S.C. 154(b) by 0 days.

(21) Appl. No.: 10/167,603

(22) Filed: Jun. 11, 2002

(65) Prior Publication Data

US 2003/0226161 A1    Dec. 4, 2003

(30) Foreign Application Priority Data

Jun. 11, 2001    (EP)    ................... 01114122

(51) Int. Cl.
*C12N 15/54*    (2006.01)
*C12N 9/10*    (2006.01)
(52) U.S. Cl. .................... 435/193; 536/23.2; 536/320.1; 536/252.3
(58) Field of Classification Search .............. 435/252.3, 435/325, 419, 254.2, 348, 193, 320; 536/23.2, 536/23.1
See application file for complete search history.

(56) References Cited

FOREIGN PATENT DOCUMENTS

CA    2231621    9/1999
WO    WO0058333    10/2000

OTHER PUBLICATIONS

H. Guo et al., "Protein Tolerance to Random Amino Acid Change", PNAS 101(25): 9205-9210. (Jun. 2004).*
Groethe, T. et al., Molecular Characterization of the Salutaridinol 7-O-Acetyltransferase Involved in Morphine Biosynthesis in Opium Poppy *Papaver somniferum, J. Biol. Chem*, 276(33):30717-30723 (2001).
Lenz, R. and M.H. Zenk, Acetyl Coenzyme A: Salutaridinol 7-O-Acetyltransferase from *Papaver somniferum* Plant Cell Cultures, *J. Biol. Chem*, 270(52):31091-31096 (1995).
Unterlinner, B. et al., Molecular cloning and functional expression of codeinone reductase: the penultimate enzyme in morphine biosynthesis in the opium poppy *Papaver somniferum, The Plant Journal*, 18(5):465-475 (1999).
Novak, B. H., et al., Morphine-Synthesis and Biosynthesis—An Update, *Current Organic Chemistry*, 4:343-362 (2000).
Rice, K. C., Synthetic Opium Alkaloids and Derivatives. A Short Total Synthesis of (±)-Dihydrothenainone, (±)-Dihydrocodeinone, and (±)-Nordihydrocodeinone as an Approach to a Practical Synthesis of Morphine, Codeine, and Congeners *J. Org. Chem*. 45:3135-3137 (1980).
Kutchan, T. M., Molecular Genetics of Plant Alkaloid Biosynthesis, in *The Alkaloids*, vol. 50 (Cordell, G., ed.) Academic Press, San Diego, pp. 257-316 (1998).
De-Eknamkul, W., and M.H. Zenk, Purification and Properties of 1,2-Dehydroreticuline Reductase from *Papaver somniferum* Seedlings, *Phytochemistry* 31:813-821 (1992).
Gerardy, R., and M.H. Zenk,, Purification and Caracterization of Salutaridine: NADPH 7-Oxidoreductase From *Papaver somniferum, Phytochemistry* 34:125-132 (1993).
Lenz, R. and M.H. Zenk, Purification and Properties of codeinone reductase (NADPH) from *Papaver somniferum* cell cultures and differentiated plants, *Eur. J. Biochem*, 233:132-139 (1995).
Gerardy, R., and M.H. Zenk, Formation of Salutaridine From (R)-Reticuline by a Membrane-Bound Cytochrome P-450 Enzyme From *Papaver somniferum, Phytochemistry* 32:79-86 (1993).
Pfitzner, A., and J. Stöckigt, Biogenetic Link Between Sarpagine and Ajmaline Type Alkaloids, *Tetrahedron Lett*. 24:5197-5200 (1983).
Fahn, W., et al., Late enzymes of vindoline biosynthesis. Actyl-CoA: 17-O-deacetylvindoline 17-O-acetyl-transferase, *Plant Cell Rep*. 4:333-336 (1985).
De Luca, V., et al., Acetyl Coenzyme A: Deacetylvindoline O-Acetyltransferase, A Novel Enzyme fro *Catharanthus, J. Plant Physiol*. 121:417-428 (1985).
Huang, F.-C., and T.M. Kutchan, Distribution of morphinan and benzo[c]phenanthridine alkaloid gene transcript accumulation in *Papaver somniferum, Phytochemistry* 53:555-564 (2000).
Linsmaier, E. M., and F. Skoog, Organic Growth Factor Requirements of Tobacco Tissue Clutures, *Physiol. Plant*. 18:100-127 (1965).
Dittrich, H. and T.M. Kutchan, Molecular cloning, expression, and induction of berberine bridge enzyme, an enzyme essential to the formation of benzophenanthridine alkaloids in the response of plants to pathogenic attack, *Proc. Natl. Acad. Sci. USA* 88:9969-9973 (1991).
Eckerskorn, C. and F. Lottspeich, Internal Amino Acid Sequence Analysis of Proteins Separated by Gel Electrophoresis after Tryptic Digestion in Polyacrylamide Matrix, *Chromatographia* 28:92-94 (1989).

(Continued)

*Primary Examiner*—Rebecca Prouty
(74) *Attorney, Agent, or Firm*—Thompson Coburn LLP; Charles P. Romano, Senior Patent Agent

(57) ABSTRACT

This invention provides: (A) a protein the sequence of which is in FIG. 8 (SEQ. ID n° 14), or a fragment thereof having at least 15 amino acids, or a variant thereof, having at least 70% identity with FIG. 8 (SEQ. ID n° 14) over a length of at least 400 amino acids; (B) a peptide comprising a fragment of salutaridinol 7-O-acetyltransferase of at least 6 consecutive amino acids not present in other plant acetyltransferases as in FIG. 2 (SEQ. IDs n° 8 to 12); (C) a nucleic acid (i) the sequence of which is in FIG. 9 (SEQ. ID n° 13) or FIG. 10 (SEQ. ID n° 15), or (ii) a fragment thereof of at least 45 nucleotides, or (iii) a variant thereof, having at least 70% identity with FIG. 9 (SEQ. ID n° 13) or FIG. 10 (SEQ. ID n° 15) over a length of at least 1200 bases, or (iv) a sequence complementary to (i), (ii) or (iii); or (v) the RNA equivalent of any of (i), (ii), or (iii); (D) a nucleic acid comprising a fragment of a salutaridinol 7-O-acetyltransferase gene of at least 18 consecutive nucleotides unique to the salutaridinol 7-O-acetyltransferase gene from the 5' or 3' untranslated regions in FIG. 9 (SEQ. ID n° 13), or a sequence complementary thereto. This invention also provides methods for producing pentacyclic morphinan alkaloids and thebaine.

6 Claims, 13 Drawing Sheets

OTHER PUBLICATIONS

Figure 1:
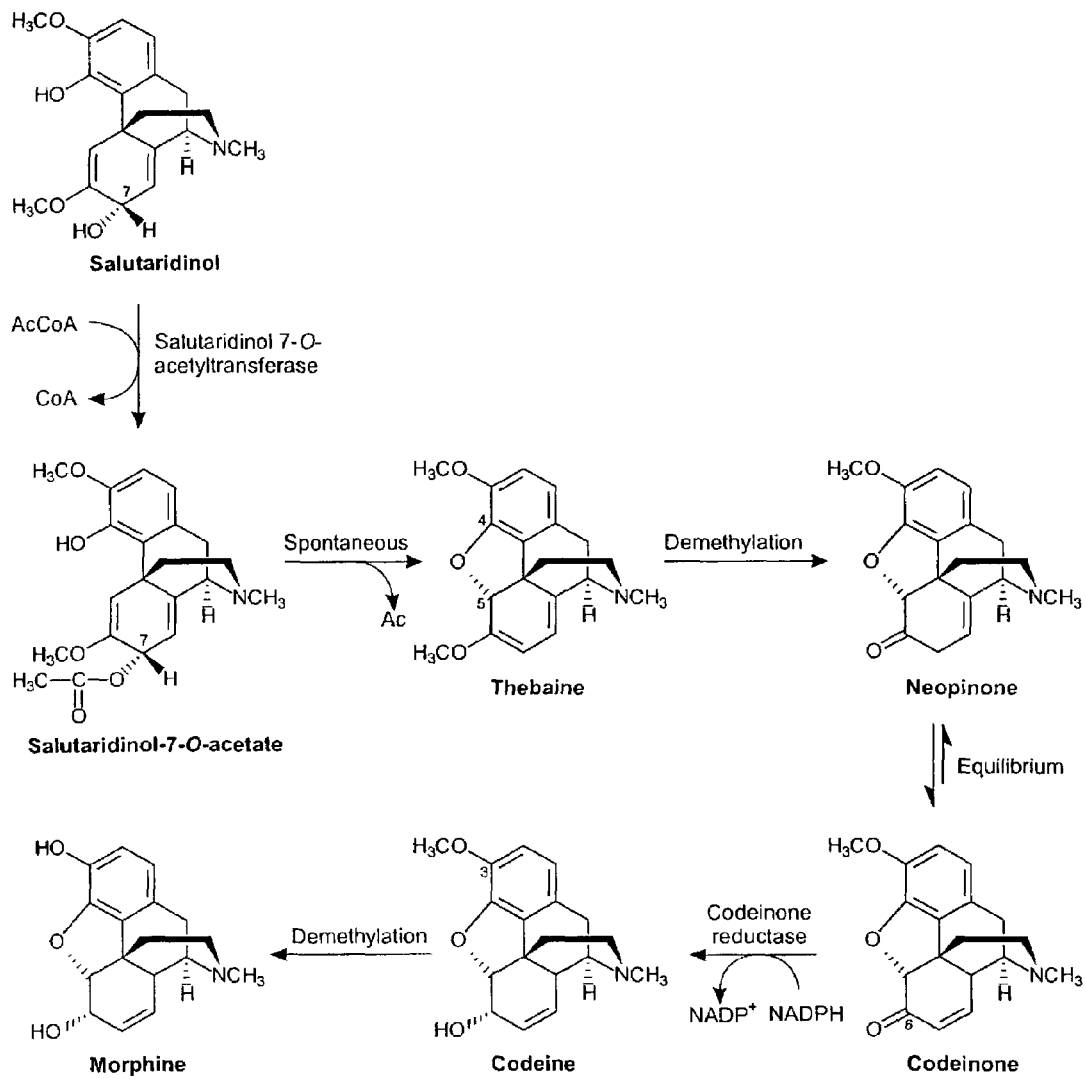

Kutchan, T. M., et al., Heterologous Expression of the Plant Proteins Strictosidine Synthase and Berberine Bridge Enzyme in Insect Cell Cultue, *Phytochemistry* 35:353-360 (1994).

Pauli, H., and T.M. Kutchan, Molecular cloning and functional heterologous expression of two alleles encoding (*S*)-N-methylcoclaurine 3'-hydroxylase (CYP80B1), a new methyl jasmonate-inducible cytochrome P-450-dependent mono-oxygenase of benzylisoquinoline alkaloid biosynthesis, *Plant J.* 13:793-801 (1998).

Roberts, M. F., et al., Location of Enzymes and Alkaloidal Metabolites in *Papaver* Latex, *Arch. Biochem. Biophys.* 222:599-609 (1983).

Decker G., et al., Characterization of proteins in latex of the opium poppy (*Papaver somniferum*) using two-dimensional gel electrophoresis and microsequencing, *Electrophoresis* 16:3500-3516 (2000).

Bracher, D., and T.M. Kutchan, Strictosidine Synthase fro *Rauvolfia serpentina*: Analysis of a Gene Involved in Indole Alkaloid Biosynthesis, *Arch. Biochem. Biophys.* 294:717-723 (1992).

St-Pierre, B., et al. The terminal *O*-acetyltransferase involved in vindoline biosynthesis defines a new class of proteins responsible for coenzyme A-dependent acyl transfer, *Plant J.* 14:703-713 (1998).

Shaw, W. V., and A.G.W. Leslie, Chloramphenicol Acetyltransferase, *Annu. Rev. Biophys. Biophys. Chem.* 20:363-386 (1991).

Hendle, J., et al., Crystallographic and Enzymatic Investigations on the Role of Ser558, His610, and Asn614 in the Catalytic Machenism of *Azobacter* vinelandii Dyhydrolipoamide Acetyltransferase (E2p), *Biochemistry* 34:4287-4298 (1995).

Miles, E. W., Modification of Histidyl Residues in Proteins by Diethylpyrocarbonate, *Methods Enzymol.* 47:431-442 (1977).

Dudareva, N., et al., Acetyl CoA: benzylalcohol acetyltransferase—an enzyme involved in floral scent production in *Clarkia breweri*, *Plant J.* 14:297-304 (1998).

Yang, Q., et al, Characterization and heterologous expression of hydroxycinnamoyl/benzoyl-CoA: anthranilate N-hydroxycinnamoyl/benzoyltransferase from elicited cell cultures of carnation, *Dianthus caryophyllus* L., *Plant Mol. Biol.* 35:777-789 (1997).

Walker, K., et al., Molecular Cloning of a Taxa-4(20),11(12)-dien-5α-ol-*O*-Acetyl Transferase cDNA from *Taxus* and Functional Expression in *Escherichia coli*, *Arch. Biochem. Biophys.* 374:371-380 (2000).

Walker, K., and R. Croteau, Molecular cloning of a 10-deacetylbaccatin III-10-*O*-acetyl transferase cDNA from *Taxus* and functional expression in *Escherichia coli*, *Proc. Natl. Acad. Sci. USA* 97:583-587 (2000).

Brown, N. F., et al., Catalytically Important Domains of Rat Carnitine Palmitoyltransferase II as Determined by Site-directed Mutagenesis and Chemical Modification, *J. Biol. Chem.* 269:19157-19162 (1994).

Sinclair, J. C., et al., Structure of arylamine N-acetyltransferase reveals a catalytic triad, *Nat. Struct. Biol.* 7:560-564 (2000).

Rush, M. D., et al., Correlation of the appearance of morphinan alkaloids and laticifer cells in germinating *Papver bracteatum* seedlings, *Plant Cell Rep.* 4:237-240 (1985).

Kutchan, T. M., et al. Cytodifferentiation and Papver Alkaloid Accumulation in J. D. Phillipson et al, eds., *The Chemistry and Biology of Isoquinoline Alkaloids*, Springer-Verlag, Berlin, pp. 281-294 (1985).

Nessler, C. L., and P.G. Mahlberg,, Laticifer Unltrastructure and Differentiation in Seedlings of Papaver bracteatum Lindl., Population Arya II (Papaveraceae), *Amer. J. Bot*. 64:541-551 (1977).

Nessler, C. L., and Mahlberg, P. G. Ontogeny and Cytochemistry of Alkaloidal Vesicles in Laticifers of Papaver somniferum L. (Papaveraceae), *Amer. J. Bot.* 65:978-983 (1978).

St-Pierre, B., et al. Multicellular Compartmentation of *Catharanthus roseus* Alkaloid Biosynthesis Predicts Intercellular Translocation of a Pathway Intermediate, *Plant Cell* 11:887-900 (1999).

Frick, S., and T.M. Kutchan, Molecular cloning and functional expression of *O*-methyltransferases common to isoquinoline alkaloid and phenylpropanoid biosynthesis, *Plant J.* 17:329-339 (1998).

Rosco, A., et al., Cloning and Heterologous Expression of NADPH-Cytochrome P450 Reductases from the Papveraceae, *Arch. Biochem. Biophys.* 348:369-377 (1997).

Hauschild K., et al., Isolation and anaylsis of a gene *bbel* encoding the berberine bridge enzyme from the California poppy *Eschscholzia californica*, *Plant Molecular Biology*, 36:473-478 (1998).

Park S. U., et al., Analysis of promoters from tyrosine/difydroxyphenylalanine decarboxylase and berberine bridge enzyme genes involved in benzylisoquinoline alkaloid biosynthesis in opium poppy, *Plant Molecular Biology*, 40:121-131 (1999).

Belny M., et al., Transformation of *Papaver somniferum* cell suspension cultures with *saml* from *A. thaliana* results in cell line of different *S*-adenosyl-L-methionine synthetase activity, *Physiologia Plantarum* 99:233-240 (1997).

Elleuch H. et al., Rice *salT* promoter is activated in *Papver somniferum* and *Nicotiana tabacum* transgenic cells in the absence of exogenous ABA, *Enzyme Microb Technol*, 29(1):106-113 (2001).

Yoshimatsu K, and K. Shimomura, Transformation of opium poppy (*Papaver somniferum* L.) with *Agrobacterium rhizogenes* MAFF 03-01724, *Plant Cell Reports*, 11:132-136 (1992).

Park S.U., and P.J. Facchini, *Agrobacterium rhizogenes*-mediated transformation of opium poppy, *Papver somniferum* L., and California poppy, *Eschscholzia californica* Cham., root cultures, *J. Exp. Botany*, 51(347):1005-1016 (2000).

Lazo, G.R., et al., A DNA transformation-competent Arabidopsis genomic library in Agrobacterium, *Bio/Technology*, 9:963-967 (1991).

Boevink P., et al., Sequence of subterranean clover stunt virus DNA: affinities with the geminiviruses, *Virology*, 207:354-361 (1995).

Marshall J.S., et al., Expression of the C4 Mel gene from *Flaveria bidentis* requires an interaction between 5' and 3' sequences, *Plant Cell*, 9:1515-1525 (1997).

Gamborg, O.L., et al., Nutrient requirements of suspension cultures of soybean root cells, *Exp. Cells Res.* 50:151-158 (1968).

* cited by examiner

FIG. 2

A)
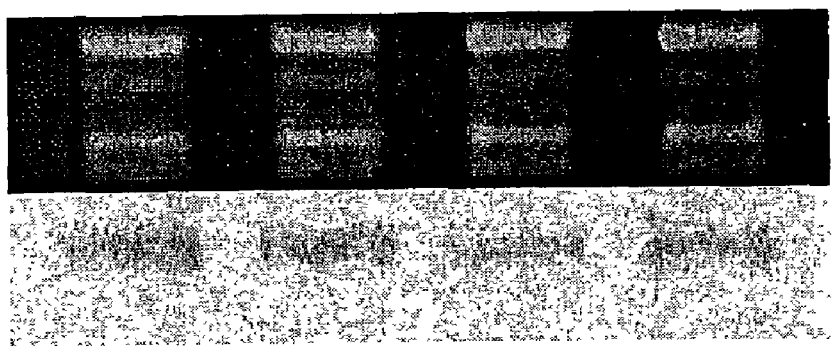
B)
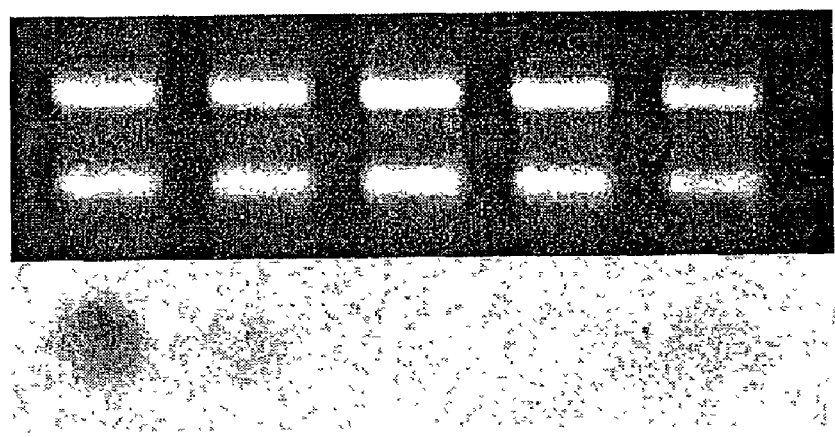
FIG. 4

TABLE 1
*Determination of $k_{cat}/K_m$ for the two alkaloidal 7-O-acetyltransferase substrates*

| Substrate | $K_m{}^a$ | $V_{max}$ | $K_{cat}$ | $K_{cat}/K_m$ |
|---|---|---|---|---|
| | µM | pmol s⁻¹ | s⁻¹ | s⁻¹µM⁻¹ |
| Salutaridinol | 9 | 25 | 4.39 | 0.49 |
| Nudaurine | 23 | 19 | 3.30 | 0.15 |

[a] apparent $K_m$

FIG. 7

MATMYSAAVEVISKETIKPTTPTPSQLKNFNLSLLDQCFPLYYYVPIILFYPATAANST
GSSNHHDDLDLLKSSLSKTLVHFYPMAGRMIDNILVDCHDQGINFYKVKIRGKMCEFMS
QPDVPLSQLLPSEVVSASVPKEALVIVQVNMFDCGGTAICSSVSHKIADAATMSTFIRS
WASTTKTSRSGGSTAAVTDQKLIPSFDSASLFPPSERLTSPSGMSEIPFSSTPEDTEDD
KTVSKRFVFDFAKITSVREKLQVLMHDNYKSRRQTRVEVVTSLIWKSVMKSTPAGFLPV
VHHAVNLRKKMDPPLQDVSFGNLSVTVSAFLPATTTTTTNAVNKTINSTSSESQVVLHE
LHDFIAQMRSEIDKVKGDKGSLEKVIQNFASGHDASIKKINDVEVINFWISSWCRMGLY
EIDFGWGKPIWVTVDPNIKPNKNCFFMNDTKCGEGIEVWASFLEDDMAKFELHLSEILE
LI

FIG. 8

1785 nucleotides

GAGAGTTTCTTCTTATCCAGCTCCTCGCAAATGAAATGATTCCATAATACCTCTCTAAAAGACTTGGTCATTA
TATAAGAGAGGGAGACCACGAGCTTCTTCTAAACAACAGAAAGTATCATCTACCATTATCAATCCTGTTAAAC
AGTTAAACACTTTGGATATATGGCAACAATGTATAGTGCTGCTGTTGAAGTGATCTCTAAGGAAACCATTAAA
CCCACAACTCCAACCCCATCTCAACTTAAAAACTTCAATCTGTCACTTCTCGATCAATGTTTTCCTTTATATT
ATTATGTTCCAATCATTCTTTTCTACCCAGCCACCGCCGCTAATAGTACCGGTAGCAGTAACCATCATGATGA
TCTTGACTTGCTTAAGAGTTCTCTTTCCAAAACACTAGTTCACTTTTATCCAATGGCTGGTAGGATGATAGAC
AATATTCTGGTCGACTGTCATGACCAAGGGATTAACTTTTACAAAGTTAAAATTAGAGGTAAAATGTGTGAGT
TCATGTCGCAACCGGATGTGCCACTAAGCCAGCTTCTTCCCTCTGAAGTTGTTTCCGCGAGTGTCCCTAAGGA
AGCACTGGTGATCGTTCAAGTGAACATGTTTGACTGTGGTGGAACAGCCATTTGTTCGAGTGTATCACATAAG
ATTGCCGATGCAGCTACAATGAGTACGTTCATTCGTAGTTGGGCAAGCACCACTAAAACATCTCGTAGTGGGG
GTTCAACTGCTGCCGTTACAGATCAGAAATTGATTCCTTCTTTCGACTCGGCATCTCTATTCCCACCTAGTGA
ACGATTGACATCTCCATCAGGGATGTCAGAGATACCATTTTCCAGTACCCCAGAGGATACAGAAGATGATAAA
ACTGTCAGCAAGAGATTTGTGTTCGATTTTGCAAAGATAACATCTGTACGTGAAAAGTTGCAAGTATTGATGC
ATGATAACTACAAAAGCCGCAGGCAAACAAGGGTTGAGGTGGTTACTTCTCTAATATGGAAGTCCGTGATGAA
ATCCACTCCAGCCGGTTTTTTACCAGTGGTACATCATGCCGTGAACCTTAGAAAGAAAATGGACCCACCATTA
CAAGATGTTTCATTCGGAAATCTATCTGTAACTGTTTCGGCGTTCTTACCAGCAACAACAACGACAACAACAA
ATGCGGTCAACAAGACAATCAATAGTACGAGTAGTGAATCACAAGTGGTACTTCATGAGTTACATGATTTTAT
AGCTCAGATGAGGAGTGAAATAGATAAGGTCAAGGGTGATAAAGGTAGCTTGGAGAAAGTCATTCAAAATTTT
GCTTCTGGTCATGATGCTTCAATAAAGAAAATCAATGATGTTGAAGTGATAAACTTTTGGATAAGTAGCTGGT
GCAGGATGGGATTATACGAGATTGATTTGGTTGGGGAAAGCCAATTTGGGTAACAGTTGATCCAAATATCAA
GCCGAACAAGAATTGTTTTTTCATGAATGATACGAAATGTGGTGAAGGAATAGAAGTTTGGGCGAGCTTTCTT
GAGGATGATATGGCTAAGTTCGAGCTTCACCTAAGTGAAATCCTTGAATTGATTTGATATTGCATTATCTACA
TGTGTTCCGTAATCATGATTTTCTCCATTTCCCTTTCCGTAGTTGGTTACAAAGAACCAAATAAAGGAAAGA
AAAAACTTGTACTGCTCGATGCTTTGACATTTTCCATGTTCATCCGTAAATTCCCATCAGAAAAGAGTTTCAA
ATATTAGGGTATTAAAAAAAAAAAAAAAAAAAA

Start position : 166
Stop position : 1588

FIG. 9

```
ATGGCAACAATGTATAGTGCTGCTGTTGAAGTGATCTCTAAGGAAACCATTAAACCCACA  60
 M  A  T  M  Y  S  A  A  V  E  V  I  S  K  E  T  I  K  P  T
ACTCCAACCCCATCTCAACTTAAAAACTTCAATCTGTCACTTCTCGATCAATGTTTTCCT  120
 T  P  T  P  S  Q  L  K  N  F  N  L  S  L  L  D  Q  C  F  P
TTATATTATTATGTTCCAATCATTCTTTTCTACCCAGCCACCGCCGCTAATAGTACCGGT  180
 L  Y  Y  Y  V  P  I  I  L  F  Y  P  A  T  A  A  N  S  T  G
AGCAGTAACCATCATGATGATCTTGACTTGCTTAAGAGTTCTCTTTCCAAAACACTAGTT  240
 S  S  N  H  H  D  D  L  D  L  L  K  S  S  L  S  K  T  L  V
CACTTTTATCCAATGGCTGGTAGGATGATAGACAATATTCTGGTCGACTGTCATGACCAA  300
 H  F  Y  P  M  A  G  R  M  I  D  N  I  L  V  D  C  H  D  Q
GGGATTAACTTTTACAAAGTTAAAATTAGAGGTAAAATGTGTGAGTTCATGTCGCAACCG  360
 G  I  N  F  Y  K  V  K  I  R  G  K  M  C  E  F  M  S  Q  P
GATGTGCCACTAAGCCAGCTTCTTCCCTCTGAAGTTGTTTCCGCGAGTGTCCCTAAGCAA  420
 D  V  P  L  S  Q  L  L  P  S  E  V  V  S  A  S  V  P  K  E
GCACTGGTGATCGTTCAAGTGAACATGTTTGACTGTGGTGGAACAGCCATTTGTTCGAGT  480
 A  L  V  I  V  Q  V  N  M  F  D  C  G  G  T  A  I  C  S  S
GTATCACATAAGATTGCCGATGCAGCTACAATGAGTACGTTCATTCGTAGTTGGGCAAGC  540
 V  S  H  K  I  A  D  A  A  T  M  S  T  F  I  R  S  W  A  S
ACCACTAAAACATCTCGTAGTGGGGGTTCAACTGCTGCCGTTACAGATCAGAAATTGATT  600
 T  T  K  T  S  R  S  G  G  S  T  A  A  V  T  D  Q  K  L  I
CCTTCTTTCGACTCGGCATCTCTATTCCCACCTAGTGAACGATTGACATCTCCATCAGGG  660
 P  S  F  D  S  A  S  L  F  P  P  S  E  R  L  T  S  P  S  G
ATGTCAGAGATACCATTTTCCAGTACCCCAGAGGATACAGAAGATGATAAAACTGTCAGC  720
 M  S  E  I  P  F  S  S  T  P  E  D  T  E  D  D  K  T  V  S
AAGAGATTTGTGTTCGATTTTGCAAAGATAACATCTGTACGTGAAAAGTTGCAAGTATTG  780
 K  R  F  V  F  D  F  A  K  I  T  S  V  R  E  K  L  Q  V  L
ATGCATGATAACTACAAAAGCCGCAGGCAAACAAGGGTTGAGGTGGTTACTTCTCTAATA  840
 M  H  D  N  Y  K  S  R  R  Q  T  R  V  E  V  V  T  S  L  I
TGGAAGTCCGTGATGAAATCCACTCCAGCCGGTTTTTTACCAGTGGTACATCATGCCGTG  900
 W  K  S  V  M  K  S  T  P  A  G  F  L  P  V  V  H  H  A  V
AACCTTAGAAAGAAAATGGACCCACCATTACAAGATGTTTCATTCGGAAATCTATCTGTA  960
 N  L  R  K  K  M  D  P  P  L  Q  D  V  S  F  G  N  L  S  V
ACTGTTTCGGCGTTCTTACCAGCAACAACAACGACAACAACAAATGCGGTCAACAAGACA  1020
 T  V  S  A  F  L  P  A  T  T  T  T  T  T  N  A  V  N  K  T
ATCAATAGTACGAGTAGTGAATCACAAGTGGTACTTCATGAGTTACATGATTTTATAGCT  1080
 I  N  S  T  S  S  E  S  Q  V  V  L  H  E  L  H  D  F  I  A
CAGATGAGGAGTGAAATAGATAAGGTCAAGGCTGATAAGGTAGCTTGGAGAAAGTCATT  1140
 Q  M  R  S  E  I  D  K  V  K  G  D  K  G  S  L  E  K  V  I
CAAAATTTTGCTTCTGGTCATGATGCTTCAATAAAGAAAATCAATGATGTTGAAGTGATA  1200
 Q  N  F  A  S  G  H  D  A  S  I  K  K  I  N  D  V  E  V  I
AACTTTTGGATAAGTAGCTGGTGCAGGATGGGATTATACGAGATTGATTTTGGTTGGGGA  1260
 N  F  W  I  S  S  W  C  R  M  G  L  Y  E  I  D  F  G  W  G
AAGCCAATTTGGGTAACAGTTGATCCAAATATCAAGCCGAACAAGAATTGTTTTTTCATG  1320
 K  P  I  W  V  T  V  D  P  N  I  K  P  N  K  N  C  F  F  M
AATGATACGAAATGTGGTGAAGGAATAGAAGTTTGGGCGAGCTTTCTTGAGGATGATATG  1380
 N  D  T  K  C  G  E  G  I  E  V  W  A  S  F  L  E  D  D  M
GCTAAGTTCGAGCTTCACCTAAGTGAAATCCTTGAATTGATTTGA  1425
 A  K  F  E  L  H  L  S  E  I  L  E  L  I  .
```

FIG. 10

```
Query: 1     ccattatcaatcctgttaaacagttaaacactttggatatATGgcaacaatgtatagtgc 60 SAT2 (C048)
             ||||||||||||||||||||||||||||||||||||||||||||||||||||||||||||
Sbjct: 126   ccattatcaatcctgttaaacagttaaacactttggatatATGgcaacaatgtatagtgc 185 SAT1 (Halle)

Query: 61    tgctgttgaagtgatctctaaggaaaccattaaacccacaactccaaccccatctcaact 120
             ||||||||||||||||||||||||||||||||||||||||||||||||||||||||||||
Sbjct: 186   tgctgttgaagtgatctctaaggaaaccattaaacccacaactccaaccccatctcaact 245

Query: 121   taaaaacttcaatctgtcacttctcgatcaatgttttcctttatattattatgttccaat 180
             ||||||||||||||||||||||||||||||||||||||||||||||||||||||||||||
Sbjct: 246   taaaaacttcaatctgtcacttctcgatcaatgttttcctttatattattatgttccaat 305

Query: 181   cattcttttctacccagccaccgccgctaatagtaccggtagcagtaaccatcatgatga 240
             ||||||||||||||||||||||||||||||||||||||||||||||||||||||||||||
Sbjct: 306   cattcttttctacccagccaccgccgctaatagtaccggtagcagtaaccatcatgatga 365

Query: 241   tcttgacttgcttaagagttctctttccaaaacactagttcacttttatccaatggctgg 300
             ||||||||||||||||||||||||||||||||||||||||||||||||||||||||||||
Sbjct: 366   tcttgacttgcttaagagttctctttccaaaacactagttcacttttatccaatggctgg 425

Query: 301   taggatgatagacaatattctggtcgactgtcatgaccaagggattaacttttacaaagt 360
             ||||||||||||||||||||||||||||||||||||||||||||||||||||||||||||
Sbjct: 426   taggatgatagacaatattctggtcgactgtcatgaccaagggattaacttttacaaagt 485

Asp
Query: 361   taaaattagaggtaaaatgtgtgacttcatgtcgcaaccggatgtgccactaagccagct 420
             |||||||||||||||||||||||| |||||||||||||||||||||||||||||||||||
Sbjct: 486   taaaattagaggtaaaatgtgtgagttcatgtcgcaaccggatgtgccactaagccagct 545
                                    Glu
                         Ile
Query: 421   tcttccctctgaaattgtttccgcgagtgtccctaaggaagcactggtgatcgttcaagt 480
             ||||||||||||| ||||||||||||||||||||||||||||||||||||||||||||||
Sbjct: 546   tcttccctctgaagttgtttccgcgagtgtccctaaggaagcactggtgatcgttcaagt 605
                         Val
                                                                Ala
Query: 481   gaacatgtttgactgtggtggaacagccatttgttcgagtgtatcacataagattgcgga 540
             |||||||||||||||||||||||||||||||||||||||||||||||||||||||| |||
Sbjct: 606   gaacatgtttgactgtggtggaacagccatttgttcgagtgtatcacataagattgccga 665
                                                                Ala Query: 541   tgcagctacaatgagtacgttcattcgtagttgggcaagcaccactaaaacatctcgtag 600
             ||||||||||||||||||||||||||||||||||||||||||||||||||||||||||||
Sbjct: 666   tgcagctacaatgagtacgttcattcgtagttgggcaagcaccactaaaacatctcgtag 725

Ala
Query: 601   tggggtgcaactgctgccgttacagatcagaaattgattccttctttcgactcggcatc 660
             |||||| |||||||||||||||||||||||||||||||||||||||||||||||||||||
Sbjct: 726   tggggttcaactgctgccgttacagatcagaaattgattccttctttcgactcggcatc 785
                 Ser Query: 661   tctattcccacctagtgaacgattgacatctccatcagggatgtcagagataccattttc 720
             ||||||||||||||||||||||||||||||||||||||||||||||||||||||||||||
Sbjct: 786   tctattcccacctagtgaacgattgacatctccatcagggatgtcagagataccattttc 845

Ser
Query: 721   cagtaccccagaggatacagaagatgataaaactgtcagcaagagatctgtgttcgattt 780
             ||||||||||||||||||||||||||||||||||||||||||||||| ||||||||||||
Sbjct: 846   cagtaccccagaggatacagaagatgataaaactgtcagcaagagatttgtgttcgattt 905
                                                          Phe Query: 781   tgcaaagataacatctgtacgtgaaaagttgcaagtattgatgcatgataactacaaaag 840
             ||||||||||||||||||||||||||||||||||||||||||||||||||||||||||||
Sbjct: 906   tgcaaagataacatctgtacgtgaaaagttgcaagtattgatgcatgataactacaaaag 965
```

FIG. 11 A

```
                Pro
Query:  841  ccgcaggccaacaagggttgaggtggttacttctctaatatggaagtccgtgatgaaatc  900
             ||||||||  |||||||||||||||||||||||||||||||||||||||||||||||||
Sbjct:  966  ccgcaggcaaacaagggttgaggtggttacttctctaatatggaagtccgtgatgaaatc  1025
                Gln Query:  901  cactccagccggttttttaccagtggtacatcatgccgtgaaccttagaaagaaaatgga  960
             ||||||||||||||||||||||||||||||||||||||||||||||||||||||||||||
Sbjct:  1026 cactccagccggttttttaccagtggtacatcatgccgtgaaccttagaaagaaaatgga  1085

Query:  961  cccaccattacaagatgtttcattcggaaatctatctgtaactgtttcggcgttcttacc  1020
             ||||||||||||||||||||||||||||||||||||||||||||||||||||||||||||
Sbjct:  1086 cccaccattacaagatgtttcattcggaaatctatctgtaactgtttcggcgttcttacc  1145

Query:  1021 agcaacaacaacgacaacaacaaatgcggtcaacaagacaatcaatagtacgagtagtga  1080
             ||||||||||||||||||||||||||||||||||||||||||||||||||||||||||||
Sbjct:  1146 agcaacaacaacgacaacaacaaatgcggtcaacaagacaatcaatagtacgagtagtga  1205

Query:  1081 atcacaagtggtacttcatgagttacatgattttatagctcagatgaggagtgaaataga  1140
             ||||||||||||||||||||||||||||||||||||||||||||||||||||||||||||
Sbjct:  1206 atcacaagtggtacttcatgagttacatgattttatagctcagatgaggagtgaaataga  1265

Query:  1141 taaggtcaagggtgataaaggtagcttggagaaagtcattcaaaattttgcttctggtca  1200
             ||||||||||||||||||||||||||||||||||||||||||||||||||||||||||||
Sbjct:  1266 taaggtcaagggtgataaaggtagcttggagaaagtcattcaaaattttgcttctggtca  1325

Query:  1201 tgatgcttcaataaagaaaatcaatgatgttgaagtgataaacttttggataagtagctg  1260
             ||||||||||||||||||||||||||||||||||||||||||||||||||||||||||||
Sbjct:  1326 tgatgcttcaataaagaaaatcaatgatgttgaagtgataaacttttggataagtagctg  1385

Query:  1261 gtgcaggatgggattatacgagattgattttggttggggaaagccaatttgggtaacagt  1320
             ||||||||||||||||||||||||||||||||||||||||||||||||||||||||||||
Sbjct:  1386 gtgcaggatgggattatacgagattgattttggttggggaaagccaatttgggtaacagt  1445

Query:  1321 tgatccaaatatcaagccgaacaagaattgttttttcatgaatgatacgaaatgtggtga  1380
             ||||||||||||||||||||||||||||||||||||||||||||||||||||||||||||
Sbjct:  1446 tgatccaaatatcaagccgaacaagaattgttttttcatgaatgatacgaaatgtggtga  1505

Query:  1381 aggaatagaagtttgggcgagctttcttgaggatgatatggctaagttcgagcttcacct  1440
             ||||||||||||||||||||||||||||||||||||||||||||||||||||||||||||
Sbjct:  1506 aggaatagaagtttgggcgagctttcttgaggatgatatggctaagttcgagcttcacct  1565

Query:  1441 aagtgaaatccttgaattgatttgatattgcattatctacatgtgttccgtaatcatgat  1500
             ||||||||||||||||||||||||||||||||||||||||||||||||||||||||||||
Sbjct:  1566 aagtgaaatccttgaattgatttgatattgcattatctacatgtgttccgtaatcatgat  1625

Query.  1501 tttctccatttccc  1514
             ||||||||||||||
Sbjct·  1626 tttctccatttccc  1639
```

FIG. 11 B

SALUTARIDINOL 7-O-ACETYLTRANSFERASE AND DERIVATIVES THEREOF

The present invention relates to proteins having salutaridinol 7-O-acetyltransferase activity and to derivatives and analogs of these proteins. The invention also relates to nucleic acid molecules encoding the proteins, derivatives and analogs, and to their use in the production of plants having altered alkaloid profiles.

The opium poppy *Papaver somniferum* produces some of the most widely used medicinal alkaloids. The narcotic analgesic morphine and the antitussive and narcotic analgesic codeine are the most important physiologically active alkaloids from this plant. Nineteen total syntheses of morphine have been reported through 1999 (1). The most efficient synthesis of morphine proceeded on medium scale with an overall yield of 29% (2). Despite many years of excellent synthetic organic chemistry concentrated on morphinans, a commercially feasible total chemical synthesis has not yet been achieved for morphine or codeine.

The enzymatic synthesis of morphine in *P. somniferum* has been almost completely elucidated by M. H. Zenk and coworkers and is summarized by Kutchan (3). Morphine is derived from two molecules of the amino acid L-tyrosine in a series of at least seventeen enzymatic steps. The latter steps in the pathway that lead specifically from (S)-reticuline, a central intermediate of isoquinoline alkaloid biosynthesis, to morphine involve three NADPH-dependent oxidoreductases (4-6), most probably three cytochromes P-450 (7) and an acetyl CoA-dependent acetyltransferase (8).

Acetyl CoA-dependent acetyltransferases have an important role in plant alkaloid metabolism. They are involved in the synthesis of monoterpenoid indole alkaloids in medicinal plant species such as *Rauwolfia serpentina*. In this plant the enzyme vinorine synthase transfers an acetyl group from acetyl CoA to 16-epi-vellosimine to form vinorine. This acetyl transfer is accompanied by a concomitant skeletal rearrangement from the sarpagan- to the ajmalan-type (9). An acetyl CoA-dependent acetyltransferase also participates in vindoline biosynthesis in *Catharanthus roseus*, the source of the chemotherapeutic dimeric indole alkaloid vinblastine (10, 11). Acetyl CoA:deacetylvindoline 4-O-acetyltransferase catalyzes the last step in vindoline biosynthesis.

Central to morphine biosynthesis in *P. somniferum* is acetyl CoA:salutaridinol 7-O-acetyltransferase [EC 2.3.1.150] (FIG. 1). Acetylation of the phenanthrene salutaridinol is followed by allylic syn-displacement of the acetylated (activated) hydroxyl by the phenolic hydroxyl, which follows stereocontrol for $S_N2'$ substitution of cyclohexene rings, thereby producing the pentacyclic morphinan ring system (8).

Each of the known enzymes of morphine biosynthesis has been detected in both *P. somniferum* plants and cell suspension culture, yet plant cell cultures have never been shown to accumulate morphine or codeine (3). Morphine accumulation in the plant appears to be related to differentiation of a latex system (12). Efforts aimed at the metabolic engineering of the *P. somniferum* alkaloid profile as well as at developing alternate biotechnological sources of morphinans, have to date been hampered by lack of knowledge regarding suitable genetic targets. Indeed, only one gene specific to the morphine biosynthesis pathway has been isolated and characterized to date (13).

The present invention provides and characterises both at the DNA and protein level, such a genetic target, namely salutaridinol 7-O-acetyltransferase (SalAT) of morphine biosynthesis in *P. somniferum*. Derivatives and variants of the protein are also provided.

More specifically, the present invention relates to a protein comprising or consisting of:
i) the amino acid sequence illustrated in FIG. 8 (SEQ. ID No. 14) or,
ii) a fragment of the amino acid sequence illustrated in FIG. 8 (SEQ. ID No. 14), said fragment having at least 10 and preferably at least 15 amino acids, or
iii) a variant of the amino acid sequence of FIG. 8 (SEQ. ID No. 14), said variant having at least 70% identity with the amino acid sequence of FIG. 8 (SEQ. ID No. 14) over a length of at least 400 amino acids.

A first preferred embodiment of the invention thus comprises the full length salutaridinol 7-O-acetyltransferase protein whose amino acid sequence is shown in FIG. 8 (SalAT 1) (SEQ. ID No. 14). The protein of the invention as illustrated in FIG. 8 has 474 amino acids, and a molecular weight of approximately 52.6 kDa (Genebank accession No.AAK73661). According to this embodiment of the invention, the full length *P. somniferum* enzyme may be obtained by isolation and purification to homogeneity from cell suspension culture, or from plant parts of *P. somniferum*, at any stage of development, and from latex of mature or immature plants. Alternatively, the enzyme may be produced by recombinant means in suitable host cells such as plant cells or insect cells. The protein may consist exclusively of those amino acids shown in FIG. 8 (SEQ. ID No. 14), or may have supplementary amino acids at the N- or C-terminus. For example, tags facilitating purification may be added. The protein may also be fused at the N- or C-terminus to a heterologous protein.

The protein whose sequence is illustrated in FIG. 8 (SEQ. ID No. 14) has salutaridinol 7-O-acetyltransferase activity.

In the context of the present invention, "salutaridinol 7-O-acetyltransferase activity" signifies the capacity of a protein to acetylate 7(S)-salutaridinol at the C7 position to give salutaridinol-7-O-acetate. This latter compound undergoes spontaneous allylic elimination at pH 8-9, leading to the formation of thebaine. At pH 7, the allylic elimination leads to dibenz [d,f]azonine alkaloids containing a nine-membered ring. Salutaridinol 7-O-acetyltransferase activity is assayed according to Lenz and zenk (8). Specifically, an enzyme solution is combined with salutaridinol and acetyl coenzyme A. Enzyme activity is determined, either by decrease of salutaridinol, or by production of thebaine at pH 8-9.

According to a second embodiment of the invention, the protein may comprise or consist of a fragment of the amino acid sequence illustrated in FIG. 8 (SEQ. ID No. 14), wherein said fragment has a length of at least 10 amino acids, preferably at least 12, or at least 15 or at least 20 amino acids. By protein "fragment" is meant any segment of the full length sequence of FIG. 8 (SEQ. ID No. 14) which is shorter than the full length sequence. The fragment may be a C- or N-terminal fragment having for example approximately 10 or 15 or 20 amino acids, or may be an internal fragment having 10 to 40 amino acids. Preferably the protein fragments have a length of 15 to 470 amino acids, for example 20 to 450 amino acids, or 25 to 400 amino acids. Particularly preferred are fragments having a length of between 350 and 450 amino acids, such as the FIG. 8 (SEQ. ID No. 14) sequence having undergone truncation at the C- or N-terminal, or short peptides having a length of 10 to 25 amino acids, for example 15 to 23 amino acids.

The protein fragments of the invention may or may not have salutaridinol 7-O-acetyltransferase activity. Normally, fragments comprising at least 400, or at least 450 consecutive amino acids of the protein shown in FIG. 8 (SEQ. ID No. 14) are enzymatically active.

Figure 2:
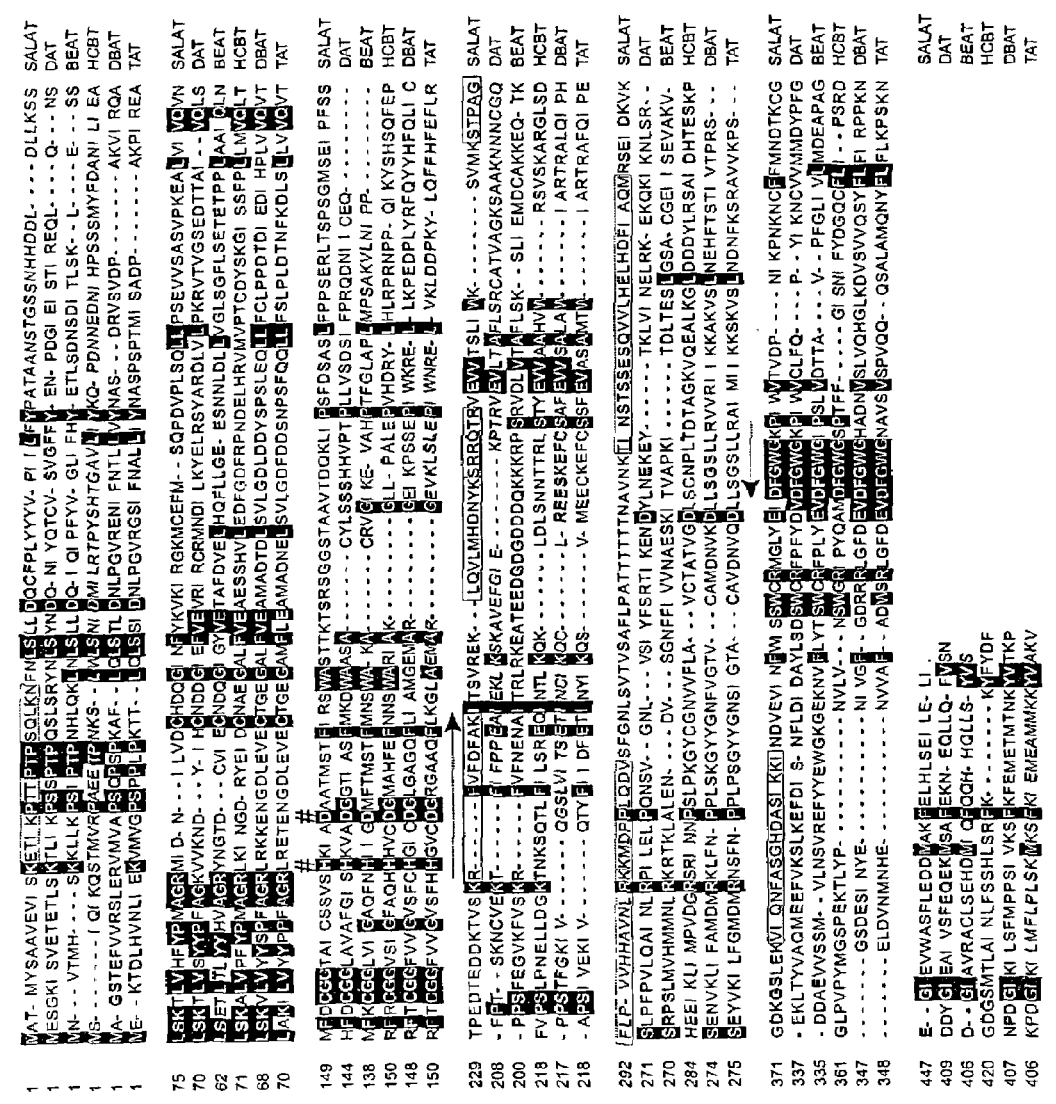

A particularly preferred class of peptides according to the invention are peptides which comprise or consist of a stretch (or "tract") of at least 5 or 6 amino acids unique to the salutaridinol 7-O-acetyltransferase protein (SalAT) illustrated in FIG. 8 (SEQ. ID No. 14). By "unique to SalAT" is meant a tract of amino acids which is not present in other plant acetyltransferases as illustrated in FIG. 2 (SEQ. ID Nos. 8 to 12). These SalAT-specific peptides typically have a length of 8 to 100 amino acids, for example 10 to 50 amino acids, or 15 to 20 amino acids. Such peptides can be used for generation of SalAT-specific antibodies for immunodetection and immunopurification techniques. Examples of such short peptides are shown as white boxes in FIG. 2.

In general, the fragments may consist exclusively of part of the FIG. 8 (SEQ. ID No. 14) sequence. Alternatively, they may additionally comprise supplementary amino acids which are heterologous to the illustrated *P. somniferum* enzyme, for example N- and/or C-terminal extensions. Such supplementary amino acids may be amino acids from salutaridinol 7-O-acetyltransferase enzymes from species other than *P. somniferum*, thus providing a chimeric salutaridinol 7-O-acetyltransferase enzyme, or may be purification tags, fusion proteins etc.

According to a third preferred embodiment of the invention, the protein comprises or consists of a variant of the amino acid sequence of FIG. 8 (SEQ. ID No. 14). By "variant" is meant a protein having at least 70% identity, and preferably at least 80% or 85% identity with the amino acid sequence of FIG. 8 over a length of at least 400 amino acids. Particularly preferred are variants having at least 90% or at least 95% identity, for example 95.5 to 99.9% identity. Preferred variants have sequences which differ from the amino acid sequence illustrated in FIG. 8 (SEQ. ID No. 14) by insertion, replacement and/or deletion of at least one amino acid, for example insertion, replacement and/or deletion of one to 10 amino acids, or one to five amino acids. Variants differing from the FIG. 8 (SEQ. ID No. 14) sequence by one to ten amino acid replacements are particularly preferred, for example two, three, four or five amino acid substitutions. Such variants may or may not have salutaridinol 7-O-acetyltransferase activity, as defined previously. Preferably, the variants have this activity.

Particularly preferred "variant" proteins of the invention are allelic variants of SalAT, or SalAT proteins arising from expression of other members of a SalAT gene family. The inventors have demonstrated that within a given species of Papaver there exist variants of the SalAT gene containing a number of single point polymorphisms, some of which give rise to changes in amino acid sequence. Typically, these variants contain one to fifteen amino acid substitutions, for example one to ten, or one to six, with respect to the FIG. 8 (SEQ. ID No. 14) sequence. Amino acid changes are usually conservative, with a neutral amino acid such as isoleucine or serine being replaced by another neutral amino acid such as valine or alanine, or an acidic amino acid such as aspartic acid being replaced by another acidic amino acid such as glutamic acid etc. SalAT activity is usually conserved. An example of an allelic variant is the enzyme shown in FIG. 11 (SEQ. ID No. 17), having five amino acid differences with respect to the FIG. 8 (SEQ. ID No. 14) sequence. The protein illustrated in FIG. 8 (SEQ. ID No. 14) will be referred to as SalAT 1, and the variant shown in FIG. 11 (SEQ. ID No. 17) as SalAT 2.

The protein variants of the *P. somniferum*. These variants, which again have at least 70% identity with the amino acid sequence of FIG. 8 (SEQ. ID No. 14) over a length of at least 400 amino acids, preferably contain the conserved amino acids shown as black boxes in FIG. 2 (SEQ. ID Nos. 7 to 12). Indeed, the amino acid sequence of the *P. somniferum* enzyme is similar to acyltransferases involved in monoterpenoid indole alkaloid-, phenylpropanoid conjugate- and diterpenoid formation (22, 26-29). Histidine and aspartate residues ($H_{163}$-XXX-$D_{167}$) are highly conserved as well as a DFGWG motif near the carboxy terminus of the proteins. The invention thus also includes variants of the FIG. 8 (SEQ. ID No. 14) protein having the required degree of identity with the FIG. 8 protein (at least 70%) and including the DFGWG motif and the ($H_{163}$-XXX-$D_{167}$) motif. The equivalent histidine residue has been shown through site directed mutagenesis or chemical modification to be essential for catalytic activity in other acyltransferases (30). Carbethoxylation of histidine residues in salutaridinol 7-O-acetyltransferase with DEPC resulted in a loss of enzyme activity. Preincubation of the enzyme with acetyl CoA partially protected a putative active site histidine residue from chemical modification and resultant inactivation. A catalytic triad (Ser-His-Asp) as found in serine proteases and lipases has been postulated for other acyltransferases (30). The crystal structure of arylamine N-acetyltransferase from *Salmonella typhimurium* indicates that a cysteine residue may be a component of the catalytic triad ($C_{69}$, $H_{107}$, $D_{122}$) (31). The amino acid sequence of salutaridinol 7-O-acetyltransferase contains both a conserved serine ($S_{33}$) and a conserved cysteine ($C_{152}$) suggesting that a catalytic triad could also be essential to enzyme activity in this family of plant acyltransferases. This consensus information assists in the identification and isolation of additional members of this family that may be involved in other plant secondary pathways.

The enzymatically active proteins of the invention, whether they are variants or fragments as defined above, or the native *P. somniferum* enzyme shown in FIG. 8 (SEQ. ID No. 14), can be used for the in vitro production of alkaloids, particularly five-ringed morphinan alkaloids, such as thebaine. For example, according to the invention, thebaine can be produced by:
  i) contacting a protein of the invention having salutaridinol 7-O-acetyltransferase activity with salutaridinol and acetyl co-enzyme A in vitro at pH 8 to 9, and
  ii) recovering the thebaine thus produced.

The SalAT proteins used in this in vitro method are generally used in purified form.

In addition to the proteins described above, the invention also relates to nucleic acid molecule encoding such proteins, for example cDNA, RNA, genomic DNA, synthetic DNA.

Examples of particularly preferred nucleic acid molecules are molecules comprising or consisting of:
  i) the nucleic acid sequence illustrated in FIG. 9 (SEQ. ID No. 13) or FIG. 10 (SEQ. ID No. 15), or
  ii) a fragment of the nucleic acid sequence illustrated in FIG. 9 (SEQ. ID No. 13) or FIG. 10 (SEQ. ID No. 15), said fragment having a length of at least 18 nucleotides, preferably at least 30 nucleotides, and most preferably at least 45 nucleotides, or
  iii) a variant of the sequence illustrated in FIG. 9 (SEQ. ID No. 13) or FIG. 10 (SEQ. ID No. 15), said variant having at least 70% identity with the sequence of FIG. 9 (SEQ. ID No. 13) or 10 (SEQ. ID No. 15), over a length of at least 1200 bases, or
  iv) a sequence complementary to sequences (i), (ii) or (iii), or
  v) the RNA equivalent of any of sequences (i), (ii), (iii) or (iv).

The nucleic acid molecules (i), (ii), (iii), (iv) and (v) are also referred to herein collectively as "the acetyltranferase gene or derivatives thereof".

The nucleic acid molecule illustrated in FIG. 10 (SEQ. ID No. 15) is the coding region of the full length cDNA of *P. somniferum* salutaridinol 7-O-acetyltransferase (Genebank accession No.AF339913). The invention encompasses any nucleic acid molecule which consists exclusively of this sequence, or which additionally includes further nucleotides at either the 5' and/or 3' extremities, for example, the sequence shown in FIG. 9 (SEQ. ID No. 13), which includes 5' and 3' untranslated regions. The additional nucleotides may be other untranslated regions, or endogenous or exogenous regulatory sequences, or fusions to other coding regions.

Also within the scope of the invention are molecules comprising or consisting of fragments of the nucleic acid sequence illustrated in FIG. 10 (SEQ. ID No. 15), said fragments having a length of at least 18 nucleotides, preferably 30 nucleotides, and most preferably at least 45 nucleotides, for example at least 60 or at least 90 nucleotides. In the context of the invention, a nucleic acid "fragment" signifies any segment of the full length sequence of FIG. 10 (SEQ. ID No. 15) which is shorter than the full length sequence.

The fragment may be a 5'- or 3'-terminal truncation for example a fragment of approximately 30 to 60 nucleotides, or an internal fragment. Preferred fragments have a length of 30 to 1400 nucleotides, for example 50 to 1200 or 70 to 1000 nucleotides. Shorter fragments having a length of 18 or 30 to 150 nucleotides can be used as primers in nucleic acid amplification reactions, enabling the isolation of related acetyltransferases of species other than *P. somniferum*, or of different lines within a given species of Papaver. When the nucleic acid fragment of the invention is relatively short, i.e. between approximately 18 to 50 nucleotides, it usually comprises a stretch (or tract) of at least 18 nucleotides which is unique to the SalAT gene. Such unique tracts may for example encode protein fragments which do not occur in other plant acetyltransferases as shown in FIG. 2 (SEQ. ID Nos. 8 to 12), or may be chosen from untranslated regions. These fragments, or their complementary sequences, are useful in amplification reactions.

A preferred example of such SalAT-specific fragments are fragments which comprise or consist of a tract of at least 18 or 20 consecutive nucleotides chosen from the 5' or 3' untranslated regions of the sequence illustrated in FIG. 9 (SEQ. ID No. 13), or a sequence which is complementary thereto.

The longer nucleic acid fragments of the invention, which have a length of about 1200 to 1400 nucleotides, generally code for proteins which are enzymatically active and can therefore be used in the same manner as the full length cDNA, for example in transformation of plant cells for production of alkaloids in vivo or in culture.

Molecules comprising fragments of the FIG. 10 (SEQ. ID No. 15) sequence also include genomic DNA which may contain at least one intron, and which can thus be considered to be an assembly of fragments linked by one or more intronic sequences. Such a genomic molecule may further comprise the endogenous SalAT regulatory sequences.

The nucleic acid molecules of the invention may also be variants of the sequence illustrated in FIG. 10 (SEQ. ID No. 15), said variants having at least 70% identity, and preferably at least 80%, at least 90% or at least 95% identity with the sequence of FIG. 10 (SEQ. ID No. 15), over a length of at least 1200 bases. Particularly preferred variants show 95 to 99.9% identity for example 96 to 99.5% identity. Most preferred variants differ from the sequence of FIG. 10 (SEQ. ID No. 15) by insertion, replacement and/or deletion of at least one nucleotide, for example replacement of one to two hundred nucleotides, or insertion of a total of 2 or more nucleotides, for example an insertion of 3 to 100 nucleotides, whilst conserving at least 70% identity with the FIG. 10 (SEQ. ID No. 15) sequence. An example of a sequence variant is a sequence that is degenerate with respect to the sequence illustrated in FIG. 10 (SEQ. ID No. 15).

Typically, nucleic acid variants of the invention have the capacity to hybridise to the sequence illustrated in FIG. 10 (SEQ. ID No.15) in stringent conditions. Stringent conditions are for example those set out in Sambrook et al., Molecular Cloning: A Laboratory Manual, Cold Spring Harbor Laboratories, Cold Spring Harbor, N.Y., USA, 1989 pages 387-389, paragraph 11.

Particularly preferred nucleic acid variants of the invention are variants of the SalAT gene occurring within a given species of alkaloid poppy, such as allelic variants or gene family members. Allelic variants usually have upto 1% difference in nucleotide sequence with respect to the full length coding sequence, for example with respect to the nucleotide sequence shown in FIG. 10 (SEQ. ID No. 15), and usually share the same chromosomal location. The sequence of FIG. 11 (SEQ. ID No. 17) (SAT 2 CO48) is thought to be such a variant, arising from a polymorphism of the SalAT gene. Members of a gene family usually differ by upto 5% with respect to the reference sequence and need not share the same chromosomal location. The nucleic acid variants according to this aspect of the invention are characterised in that they comprise at least one nucleic acid substitution with respect to the FIG. 10 (SEQ. ID No. 15) sequence, for example 2 to 30 base changes. The changes are usually single base changes and may be silent or may give rise to amino acid differences.

The different polymorphic forms of the SalAT gene, such as alleles or gene family members, can be identified using amplification techniques with primers derived from the SalAT 1 sequence, particularly primers permitting amplification of the full coding sequence. Suitable primers include portions of the reading frame, for example sequences having a length of around 20 to 40 nucleotides and corresponding to the 5' and 3' extremities of the coding sequence, for example immediately downstream of the ATG start codon and immediately upstream of the Stop codon. Alternatively, other suitable primers correspond to parts of the 5' and 3' untranslated regions, as illustrated in the Examples below. For example, RT PCR on mRNA from an alkaloid poppy, particularly P.somniferum, can be carried out using a primer pair corresponding to a stretch of around 30 bases upstream of the ATG start codon and downstream of the stop codon in FIG. 9 (SEQ. ID No.13). These techniques permit the identification of variants of the gene within a species, for example *P. somniferum*. The primers may be adapted to allow inclusion of a restriction enzyme site on the end of the amplification product to facilitate cloning. The variants which can be identified and cloned using such techniques are within the scope of the present invention.

Nucleic acid variants and fragments of the invention may encode an enzymatically active protein or not. Preferrred variants encode proteins having salutaridinol 7-O-acetyltransferase activity, as defined previously.

The invention also encompasses nucleic acid molecules that are complementary to any of the foregoing molecules, variants and fragments. In the context of the invention, "complementary" means that Watson-Crick base-pairs can form between a majority of bases in the complementary sequence and the reference sequence. Preferably, the complementarity is 100%, but one or two mismatches in a stretch of twenty or thirty bases can be tolerated. Additionally, complementary stretches may be separated by non-complementary stretches. Particularly preferred examples of complementary sequences are antisense oligonucleotides and ribozymes, which can be used in alkaloid-producing plants such as poppies to down-regulate the production of salutaridinol 7-O-acetyltransferase, or related enzymes, thereby modifying the alkaloid profile of the plant.

The nucleic acid molecules of the invention can be used to transform or transfect eukaryotic and prokaryotic cells. To this end, the sequences are usually operably linked to transcription regulatory sequences such as promoters, transcription terminators, enhancers etc. The operable link between the acetyltransferase-derived coding sequence and the regulatory sequence(s) may be direct or indirect, i.e. with or without intervening sequences, such as internal ribosome entry sites (IRES). The regulatory sequences may be endogenous to the coding sequence, i.e. they are the regulatory sequences naturally associated with the acetyltransferase sequence in the genome of the plant. Alternatively, the regulatory sequences may be heterologous to the acetyltransferase sequence. In this latter case the resulting construct forms a chimeric gene, comprising a coding sequence derived from the acetyltransferase gene, operably linked to at least one heterologous transcription regulatory sequence. In the context of the invention, the term "coding sequence" signifies a DNA sequence that encodes a functional RNA molecule. The RNA molecule may be untranslated, or may encode an enzymatically-active protein, or enzymatically-inactive protein. Particularly preferred promoters for plant expression are constitutive promoters such as the 35S promoter, or tissue specific, or developmentally specific promoters, or inducible promoters, depending upon which expression pattern is sought.

The inventors have examined the expression pattern of SalAT in *P. somniferum*. SalAT was expressed in each major plant part analyzed—root, stem, leaf and capsule. This corresponds to the detection of transcript of another morphine biosynthesis-specific gene, cor1, in each plant organ analyzed (12). Additionally, salutaridinol 7-O-acetyltransferase and codeinone reductase enzyme activity have each been detected in the cytosolic fraction of isolated latex (12,13). The gene cyp80b1 participates in (S)-reticuline biosynthesis, occurring before a bifurcation in the biosynthetic pathway that leads to more than 80 isoquinoline alkaloids. Cyp80b1 is, therefore, common to several biosynthetic pathways including morphine, sanguinarine and noscapine. Transcript of cyp80b1 was also detected in all plant organs analyzed (12). Accumulation of morphinan alkaloids is thought to correlate with the appearance of laticifer cells in the developing plant and in differentiating plant cell culture (32,33). A reticulated laticifer system associated with the vascular tissue is present through the aerial parts of the poppy plant. In roots, non-reticulated laticifers are present (34,35). The localization of three genes of morphine biosynthesis, cyp80b1, salAT and cor1 is thus far consistent with the assumption this biosynthesis is, at least in part, associated with laticifer cells. Interestingly, deacetylvindoline acetyltransferase has been localized to laticifer cells in aerial parts of *C. roseus* (36).

The invention also relates to eukaryotic and prokaryotic cells transformed or transfected by the nucleic acid sequences derived from the acetyltransferase gene. An example of a suitable prokaryotic cell is a bacterial cell. Examples of suitable eukaryotic cells are yeast cells, vertebrate cells such as mammalian cells, for example mouse, monkey, or human cells, or invertebrate cells such as insect cells. Plant cells are particularly preferred. In the context of the present invention, the term "plant" is to be understood as including mosses and liverworts. The plant cells can be any type of plant cells, including monocotyledonous or dicotyledonous plant cells. The cells may be differentiated cells or callus for example suspension cultures. Cells of the genus *Papaver* are particularly preferred.

According to the invention, cells are transfected or transformed using techniques conventional in the art, in conditions allowing expression of the O-acetyltransferase or derivatives. A number of transformation techniques have been reported for *Papaver*. For example, microprojectile bombardment of cell suspension cultures may be used (refs. 40, 41). Transformation may also be effected using *Agrobacterium tumefaciens* (refs 42, 43), or *Agrobacterium rhizogenes*, (Refs 44, 45) using either cell suspension cultures or tissue explants. International patent application WO 9934663 also reports methods for transforming and regenerating poppy plants.

The cell type that is selected for transformation or transfection depends to a large extent upon the objective to be achieved. In fact, the nucleic acid molecules of the invention can be used to achieve a number of objectives which will be discussed below. Depending on the type of molecule introduced into the plant cell, and the metabolic pathways present in the cell, a wide range of effects can be achieved.

A first objective is to produce recombinant acetyltransferase enzyme, or derivatives thereof. A preferred method for producing proteins having salutaridinol 7-O-acetyltransferase activity comprises the steps of:
  i) transforming or transfecting a cell with a nucleic acid molecule encoding enzymatically active salutaridinol 7-O-acetyltransferase, in conditions permitting the expression of the protein having salutaridinol 7-O-acetyltransferase activity,
  ii) propagating the said cells, and
  iii) recovering the thus-produced protein having salutaridinol 7-O-acetyltransferase activity.

For the purpose of producing recombinant enzyme, any of the above listed cell-types can be used. Plant cells such as cells of a *Papaver* species, or insect cells, as demonstrated in the examples below, are particularly suitable. Bacterial cells, such as *E. coli*, can also be used.

Nucleic acid constructs which encode enzymatically active salutaridinol 7-O-acetyltransferase activity suitable for use in this method include the sequences illustrated in FIG. 9 (SEQ. ID No.13), FIG. 10 (SEQ. ID No.15) and FIG. 11 (SEQ. ID No.17), degenerate equivalents thereof, variants having at least 70% identity to the FIG. 10 (SEQ. ID No.15) sequence, variants capable of hybridizing in stringent conditions to the FIG. 10 (SEQ. ID No.15) sequence, and fragments thereof having a length of at least 1200, and preferably 1300 nucleotides. The recombinant enzyme thus produced can be used in in vitro methods for producing pentacyclic morphinan alkaloids, particularly thebaine.

A second, important aspect of the invention is a biotechnological production of thebaine, codeine and morphine.

cDNAs encoding several enzymes of morphine biosynthesis have now been isolated. The first enzyme in the biosynthetic pathway for which a cDNA was isolated is norcoclaurine 6-O-methyltransferase (37). The next is the cytochrome P-450-dependent monooxygenase (S)-N-methylcoclaurine 3'-hydroxylase (12,18). These enzymes are common to the morphine, noscapine and sanguinarine biosynthetic pathways. Specific to morphine biosynthesis are salutaridinol 7-O-acetyltransferase (reported herein) and codeinone reductase, the penultimate enzyme of the morphine pathway that reduces codeinone to codeine (13). A cDNA encoding an enzyme involved generally in metabolism, but essential to the activity of the cytochrome P-450-dependent monooxygenase, the cytochrome P-450 reductase, has also been isolated (38). Each of the cDNAs has been functionally expressed in insect cell culture (*S. frugiperda* Sf9 cells) or in *E. coli*. An immediate application of these cDNAs is in the metabolic engineering of *P. somniferum* to obtain altered alkaloid profiles in the plant. Another goal is a biomimetic synthesis of morphinan alkaloids combining chemically- and enzymatically-catalyzed steps. For this latter application, depending upon the plant-type used, additional cDNAs encoding enzymes that mediate transformations occurring between (R)-reticuline and morphine may need to be isolated and introduced.

This major objective of the invention thus relates to the use of the O-acetyltransferase genes and derivatives thereof to produce pentacyclic morphinan alkaloids, particularly thebaine, in plants or in plant cell cultures, and to alter the alkaloid profiles of alkaloid-producing plants such as poppies. In the context of the invention, the term "alkaloid producing plant" signifies plants that naturally have the capacity to produce opium alkaloids, or morphinan alkaloids such as morphine, codeine, thebaine and oripavine.

For this objective, plant cells are used as host cells. For this aspect of the invention, plants that are particularly preferred are those belonging to the families Papaveraceae, Euphorbiaceae, Berberidaceae, Fumariaceae and Ranunculaceae, although other families can also be used. These families are particularly advantageous because they share at least partially, *P. somniferum's* biosynthetic pathway leading from (R)-reticuline to morphine (3). This pathway is represented diagramatically below:

For the production of pentacyclic morphinans, particulary thebaine, nucleic acid molecules encoding proteins having salutaridinol 7-O-acetyltransferase activity are introduced into plant cells which naturally already have the capacity to produce (R)-reticuline, and preferably also to produce salutaridine and/or salutaridinol. Such plants are preferred because they are highly likely to have the endogenous enzymes necessary to carry out the complete pathway from (R)-reticuline to thebaine.

Tables 2A, 2B, 2C and 2D below provide non-limiting examples of plants able to produce these different products from (R)-Reticuline. In these Tables, '+' provides a non-quantitative indication of the capacity to produce the indicated compound, '−' indicates an inability to produce the indicated compound at detectable levels, and * indicates trace levels, depending on the sensitivity of the analysis (Ref. 39):

TABLE 2A

Plants of the genus Papaver producing (R) - reticuline, salutaridine, thebaine and other pentacyclic alkaloids

| Plant | (R)-Ret. | Salutaridine | Thebaine | Codeine | Morphine |
|---|---|---|---|---|---|
| *P. bracteatum* | + | + | + | + | * |
| *P. cylindricum* | + | + | + | + | + |
| *P. orientale* | + | + | + | + | * |
| *P. setigerum* | + | + | + | + | + |
| *P. somniferum* | + | + | + | + | + |

TABLE 2B

Plants of the genus Papaver producing (R) - reticuline, salutaridine, thebaine

| Plant | (R)-Ret. | Salutaridine | Thebaine | Codeine | Morphine |
|---|---|---|---|---|---|
| *P. pseudo-orientale* | + | + | + | − | − |
| *P. lauricola* | + | + | + | − | − |
| *P. persicum* | + | + | + | − | − |
| *P. caucasium* | + | + | + | − | − |
| *P. carmeli* | + | + | + | − | − |

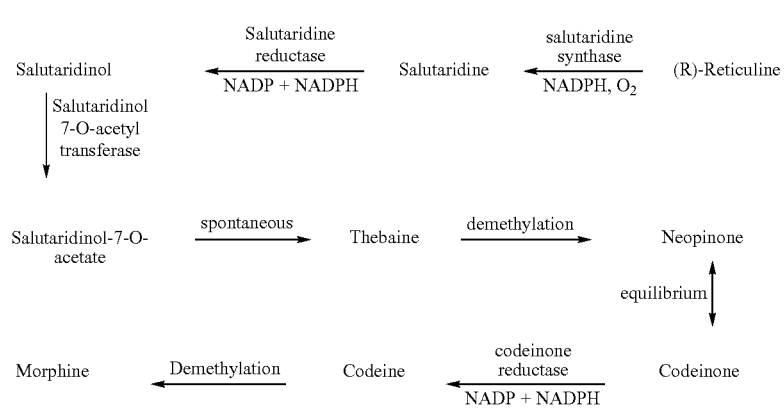

TABLE 2C

Plants producing (R) - reticuline and salutaridine

| Plant | (R) - Ret. | Salutaridine | Thebaine | Codeine | Morphine |
|---|---|---|---|---|---|
| P. acrochaetum | + | + | − | − | − |
| P. alpinum | + | + | − | − | − |
| P. armeniacum | + | + | − | − | − |
| P. atlanticum | + | + | − | − | − |
| P. aurantiacum | + | + | − | − | − |
| P. corona | + | + | − | − | − |
| P. croceum | + | + | − | − | − |
| P. curviscapum | + | + | − | − | − |
| P. degenii | + | + | − | − | − |
| P. ernesti | + | + | − | − | − |
| P. fugax | + | + | − | − | − |
| P. gracile | + | + | − | − | − |
| P. heldreichii | + | + | − | − | − |
| P. kerneri | + | + | − | − | − |
| P. lasiothrix | + | + | − | − | − |
| P. nudicaule | + | + | − | − | − |
| P. pilosum | + | + | − | − | − |
| P. polychaetum | + | + | − | − | − |
| P. rhaeticum | + | + | − | − | − |
| P. rubroaurantiacum | + | + | − | − | − |
| P. sendtneri | + | + | − | − | − |
| P. strictum | + | + | − | − | − |
| P. tartricum | + | + | − | − | − |
| P. tauricola | + | + | − | − | − |
| C. campestris[1] | + | + | − | − | − |
| C. balsamifera | + | + | − | − | − |
| C. ferruginellus | + | + | − | − | − |
| C. ruizianus | + | + | − | − | − |

[1]Members of the Croton genus (family *Euphorbiaceae*)

TABLE 2D

Plant families producing (R)-Reticuline

| Plant family | (R)-Reticuline |
|---|---|
| Berberidaceae | + |
| e.g. | |
| Berberis spp. | |
| Podophyllum spp. | |
| Fumariaceaeae | + |
| e.g. | |
| Adlumia spp. | |
| Cordyalis spp. | |
| Dicentra spp. | |
| Fumaria spp. | |
| Papaveraceae | + |
| e.g. | |
| Papaver spp. | |
| Argemone spp. | |
| Bocconia spp. | |
| Glaucium spp. | |
| Eschscholtzia spp. | |
| Ranunculaceae | + |
| e.g. | |
| Thalictrum spp. | |

According to a preferred variant, for the production of pentacyclic morphinans such as thebaine, morphine and codeine, a host plant cell is selected that naturally contains a gene encoding salutaridinol 7-O-acetyltransferase. Such plants may be identified in several ways:
  genomic DNA, cDNA or mRNA of the plant hybridises in stringent conditions to the nucleic acid molecule illustrated in FIG. 10 (SEQ. ID No.15), or a fragment or variant thereof, and/or
  the plant is capable of producing thebaine, and possibly other pentacyclic morphinan alkaloids such as morphine and codeine, and/or
  salutaridinol 7-O-acetyltransferase activity can be detected in the latex of the plant.

Specific examples of such plants are shown in Tables 2A and 2B above. The endogenous salutaridinol-7-O-acetyltransferase activity is supplemented by the introduction of an exogenous nucleic acid molecule encoding a protein having salutaridinol-7-O-acetyltransferase activity. The expression of the exogenous acetyltransferase leads to over-expression of the enzyme, and increases thebaine production. The natural alkaloid profile of the plant is thereby altered. Such alteration can take the form of an alteration in total alkaloid yield, or in the type of alkaloid, or in the relative proportions of different alkaloids, produced by the plant. For example, members of the genus *Papaver*, e.g. *P. somniferum*, can be altered using the process of the invention to produce thebaine as major or sole alkaloid.

In general, for the production of morphine and codeine, plants are preferred which have all the necessary endogenous enzymes i.e. plants that naturally produce morphine and codeine, for example those shown in Table 2A.

For the production of thebaine, it is similarly possible to use a plant cell that naturally produces substantial amounts of thebaine, whereby the thebaine produced is the result of an over-expression of acetyltransferase from both the endogenous and exogenous genes. Examples are given in Table 2A and 2B. It is however possible, for thebaine production, to use a cell of a plant that does not naturally produce substantial amounts of thebaine. According to this latter embodiment, the exogenous salutaridinol 7-O-acetyltransferase confers upon the plant or plant cell the ability to synthesize thebaine. Examples of plants which can be used in this variant of the invention are shown in Tables 2C and 2D.

As particularly preferred plants for this embodiment of the invention, members of the Papaveraceae family, particularly Papaver somniferum, Papaver bracteatum, Papaver setigerum, Papaver orientate, Papaver pseud-orientale, Papaver cylindricum can be cited.

According to a further aspect of the invention, the alkaloid profile of an alkaloid-producing plant (such as the Papaveraceae) can be altered by introducing nucleic acid molecules which have inhibitory activity on salutaridinol-7-O-acetyltransferase expression, for example molecules which are complementary to the deacetylase gene or its transcript. Antisense molecules complementary to the transcript of the sequence illustrated in FIG. 10 (SEQ. ID No.15), or a ribozyme capable of hybridising to the said transcript are examples of such inhibitory molecules. Such molecules have the capacity to inhibit functional expression of the endogenous salutaridinol-7-O-acetyltransferase, thus reducing thebaine production. The altered thebaine production results in a global modification of the alkaloid profile of the plant.

As part of the process of production of morphinans, (e.g. morphine, codeine or thebaine), the transformed or transfected cells are propagated to produce a multiplicity of morphinan-producing cells, and then conventional techniques are used to recover the pentacyclic alkaloid(s). The multiplicity of cells produced by propagation may be a cell culture of differentiated or undifferentiated cells, for example callus suspension cultures. Alternatively the cells may be regenerated to provide a whole transgenic or chimeric plant. The invention also encompasses the cell cultures and transgenic plants produced from the transformed or transfected cells. Particularly preferred are transgenic plants of the genus *Papaver*, for example those in Tables 2A and 2B, which exhibit over-expression of salutaridinol 7-O-acetyltransferase. These plants are characterised by the presence of at least one endogenous salutaridinol 7-O-acetyltransferase gene, accompanied by at least one copy of an exogenous salutaridinol 7-O-acetyltransferase gene of the invention. Typically the exogenous SalAT gene can be distinguished from the endogenous gene by the presence of heterologous transcription regulatory sequences.

Other preferred transgenic plants exhibit reduced expression of salutaridinol 7-O-acetyltransferase as a result of the introduction of a nucleic acid encoding a salutaridinol 7-O-acetyltransferase inhibitor, for example a ribozyme or an antisense molecule.

The invention also relates to the seed of the transgenic plants of the invention, and also to the opium and straw, or straw concentrates produced by the altered plants.

The morphine biosynthetic genes of the invention permit investigation of the question of why only *P. somniferum* produces morphine, while other *Papaver* species such as *P. rhoeas, P. orientate, P. bracteatum, P. nudicaule* and *P. atlanticum* do not. SalAT transcript was detected in RNA isolated from *P. somniferum, P. orientate* and *P. bracteatum*, but not in RNA from *P. nudicaule* and *P. atlanticum*. This is consistent with the expected distribution based upon accumulation of alkaloids having the morphinan nucleus in these species (i.e. morphine in *P. somniferum*, thebaine in *P. bracteatum* and oripavine in *P. orientate*). This is in sharp contrast to those results obtained for cor1 transcript, which was detected also in *Papaver* species that are not known to accumulate codeine (12). The genes of alkaloid biosynthesis in *P. somniferum* will certainly continue to provide useful information on the molecular evolution of plant secondary metabolism in latex systems.

Various aspects of the invention are illustrated in the Figures:

FIG. 1. Schematic biosynthetic pathway leading from salutaridinol to morphine in opium poppy. The 7-hydroxy moiety of salutaridinol is activated by the transfer of an acetyl group from acetyl CoA, catalyzed by salutaridinol 7-O-acetyltransferase. Elimination of acetate to form thebaine is a pH-dependent reaction that can proceed spontaneously. The demethylation of thebaine and codeine are each thought to be catalyzed by cytochrome P-450-dependent enzymes.

FIG. 2. Amino acid sequence comparison of salutaridinol 7-O-acetyltransferase to other plant acetyltransferases involved in secondary metabolism. SALAT, salutaridinol 7-O-acetyltransferase from *P. somniferum* (this work); DAT, deacetylvindoline acetyltransferase of *C. roseus* (22); BEAT, benzylalcohol acetyltransferase from *Clarkia breweri* (26), HCBT, anthranilate N-hydroxycinnamoyl/benzoyltransferase from *Dianthus caryophyllus* (27); DBAT, 10-deacetylbaccatin III-10-O-acetyltransferase and TAT, taxadienol acetyltransferase, both from *Taxus cuspidata* (28,29). Black boxes indicate conserved residues; white boxes indicate the internal peptide sequences obtained from native salutaridinol 7-O-acetyltransferase; arrows indicate the positions of the peptides used to design oligodeoxynucleotide primers for RT-PCR; # denotes positions of the highly conserved consensus sequence HXXXD (SEQ. ID Nos.7 to 12).

Figure 3:
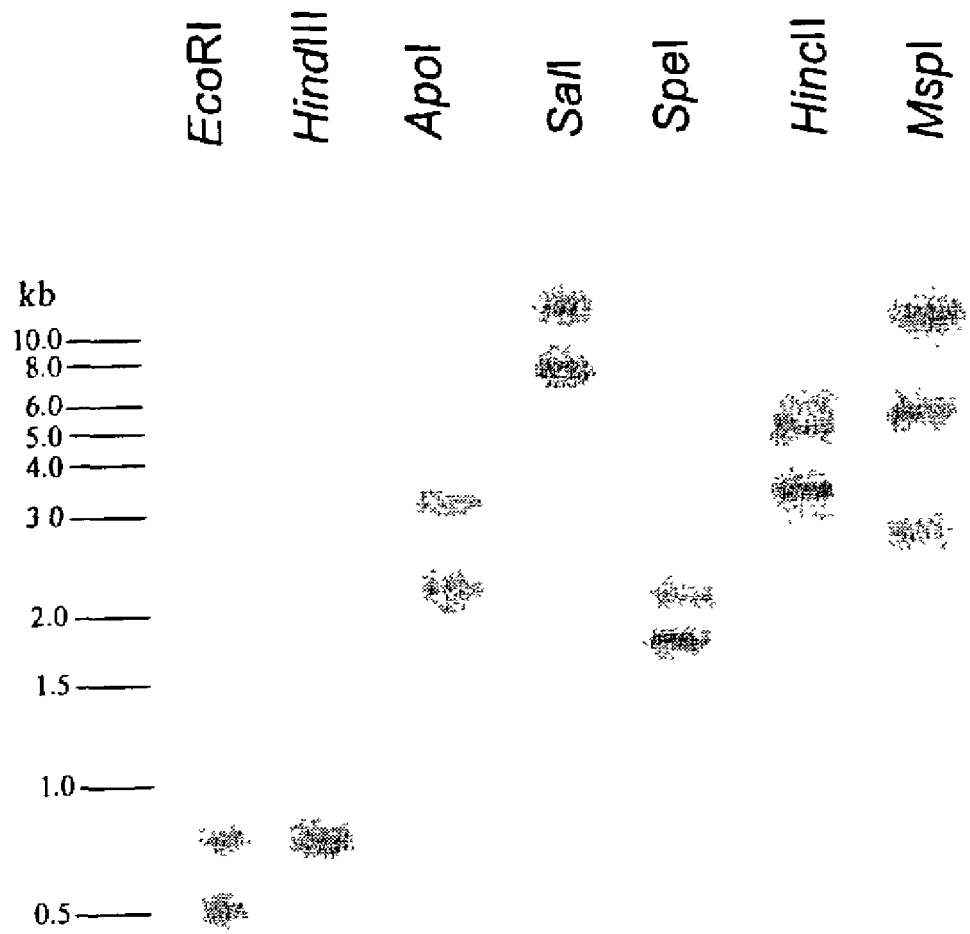

FIG. 3. Genomic DNA gel blot analysis of the salutaridinol 7-O-acetyltransferase gene in opium poppy. Genomic DNA isolated from *P. somniferum* 3-week-old seedlings was hybridized to salAT full-length cDNA and was visualized by phosphorimagery. The number of restriction endonuclease recognition sites that occur within the open reading frame are as follows: EcoRI, 0; HindIII, 0; ApoI, 1; SalI, 1; SpeI, 1; HincII, I; MspI, 3.

FIG. 4. RNA gel blot analysis of A) salAT is expressed in lane 1. root, lane 2. capsule, lane 3 stem and lane 4 leaf of the mature poppy plant and B) salAT transcript accumulation in 3-week-old seedlings of lane 1. *P. somniferum*, lane 2. *P. orientale*, lane 3. *P. atlanticum*, lane 4. *P. nudicaule*, and lane 5. *P. bracteatum*. The dark portion of each panel is a photograph of ethidium bromide visualized RNA in the gel prior to blotting. This serves as an RNA loading control. The bottom portion of each panel is the results obtained after blotting and hybridization to salAT full-length cDNA visualized by phosphorimagery.

Figure 5:
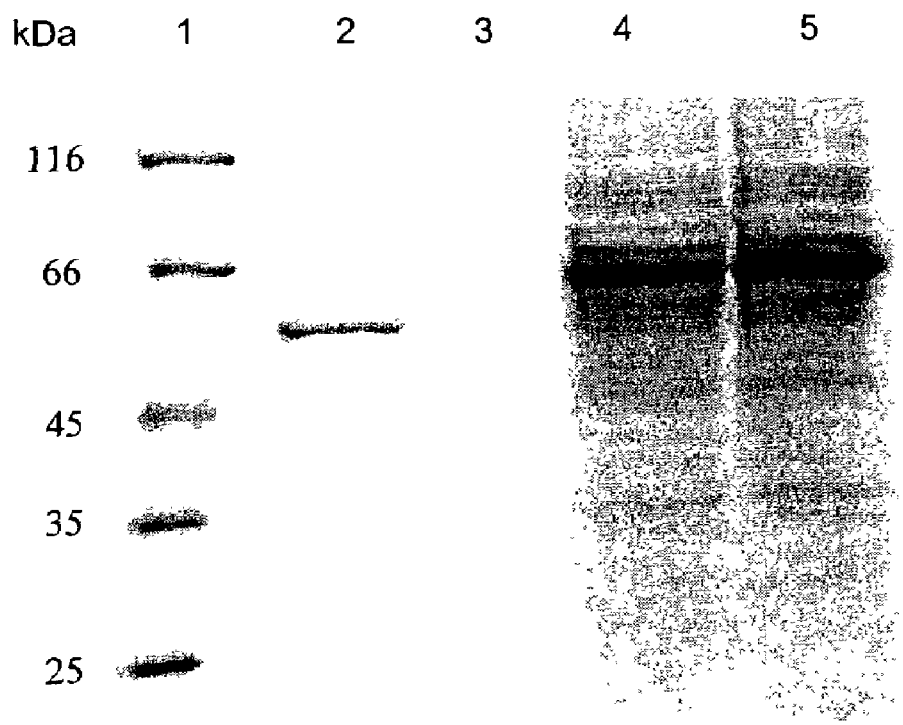

FIG. 5. SDS-PAGE analysis of fractions from the purification of recombinant salutaridinol 7-O-acetyltransferase from *S. frugiperda* Sf9 cell culture medium. Lane, 1. protein standards (MBI Fermentas), lane 2. 250 mM imadazole buffer elution of salutaridinol 7-O-acetyltransferase from the Talon resin, lane 3. 10 mM imadazole buffer wash of Talon resin, lane 4. Talon column flow-through, lane 5. Sf9 cell culture medium after ammonium sulfate precipitation and dialysis.

Figure 6:
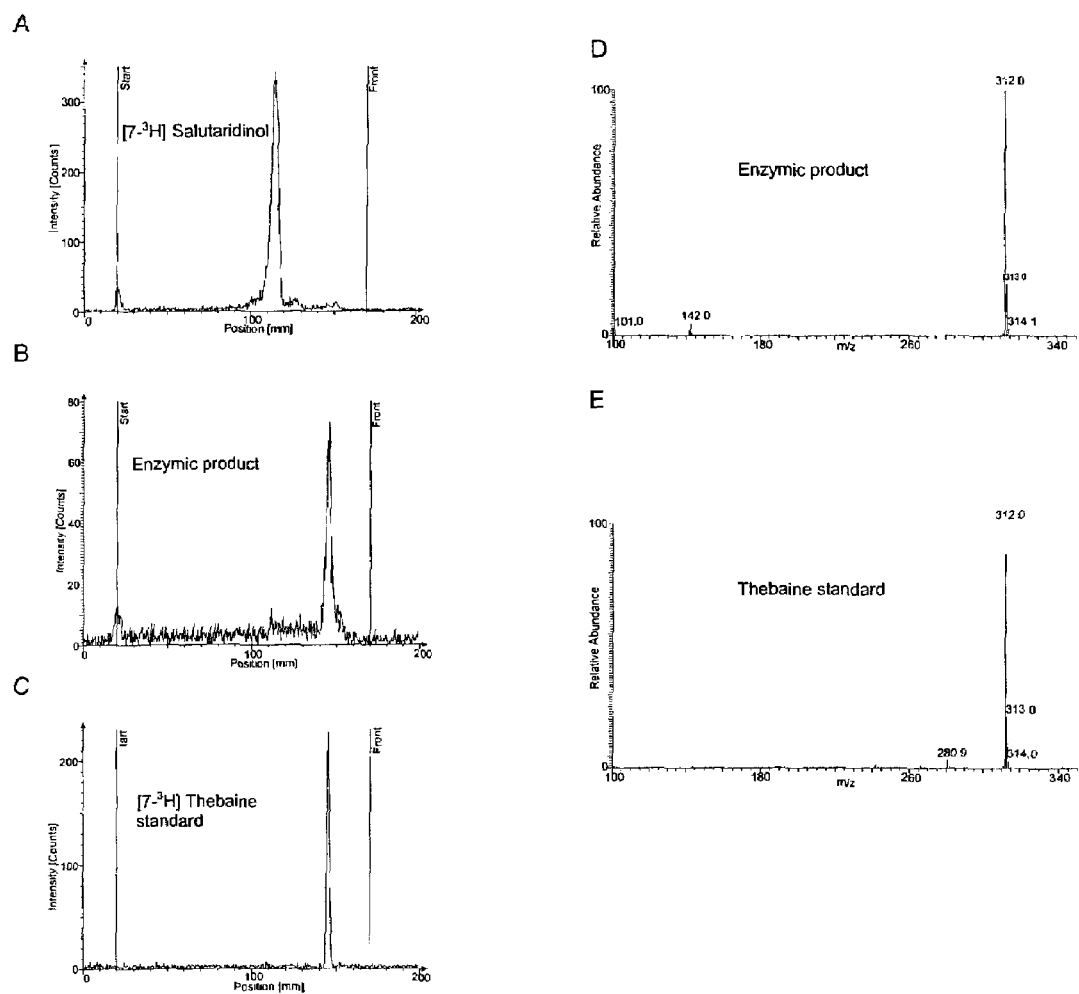

FIG. 6. TLC radio-chromatogram of an aliquot of an enzyme assay containing A) [7-$^3$H]salutaridinol, acetyl CoA and boiled enzyme, B) [7-$^3$H]salutaridinol, acetyl CoA and recombinant salutaridinol 7-O-acetyltransferase and C) [7-$^3$H]thebaine standard. D) HPLC-positive ion electrospray mass spectral analysis of the product produced in an assay containing salutaridinol, acetyl CoA and recombinant salutaridinol 7-O-acetyltransferase. E) HPLC-positive ion electrospray mass spectral analysis of thebaine standard.

FIG. 7: Table 1 as referred to in the Examples.

FIG. 8: Deduced amino acid sequence of *P. somniferum* salutaridinol 7-O-acetyltransferase. An identical match was observed between the deduced and directly determined amino acid sequences of ten internal peptides distributed throughout the open reading frame (SEQ. ID No.14).

FIG. 9: cDNA sequence of *P. somniferum* salutaridinol 7-O-acetyltransferase (1785 nucleotides). The start codon is at position 166, and the Stop at position 1588 (SEQ. ID No.13).

FIG. 10: Coding sequence of *P. somniferum* salutaridinol 7-O-acetyltransferase, showing the amino acid sequence also (SEQ. ID No.15).

FIG. 11: Alignment of cDNA sequences of *P. somniferum* salutaridinol 7-O-acetyltransferase from different sources. The top line shows cDNA cloned from *P. somniferum* cultivar CO48 (designated herein as SalAT 2 or "SAT 2 CO48" in FIG. 11 (SEQ. ID No.17)). The bottom line shows cDNA cloned from *P. somniferum* cell suspension cultures (designated herein as SalAT 1 or "SAT 1 Halle" in FIG. 11). Differences in nucleotide sequence are shown in bold type and changes in amino acid sequence are above and below the nucleic acid sequences (SEQ. ID No.17)

Figure 12:
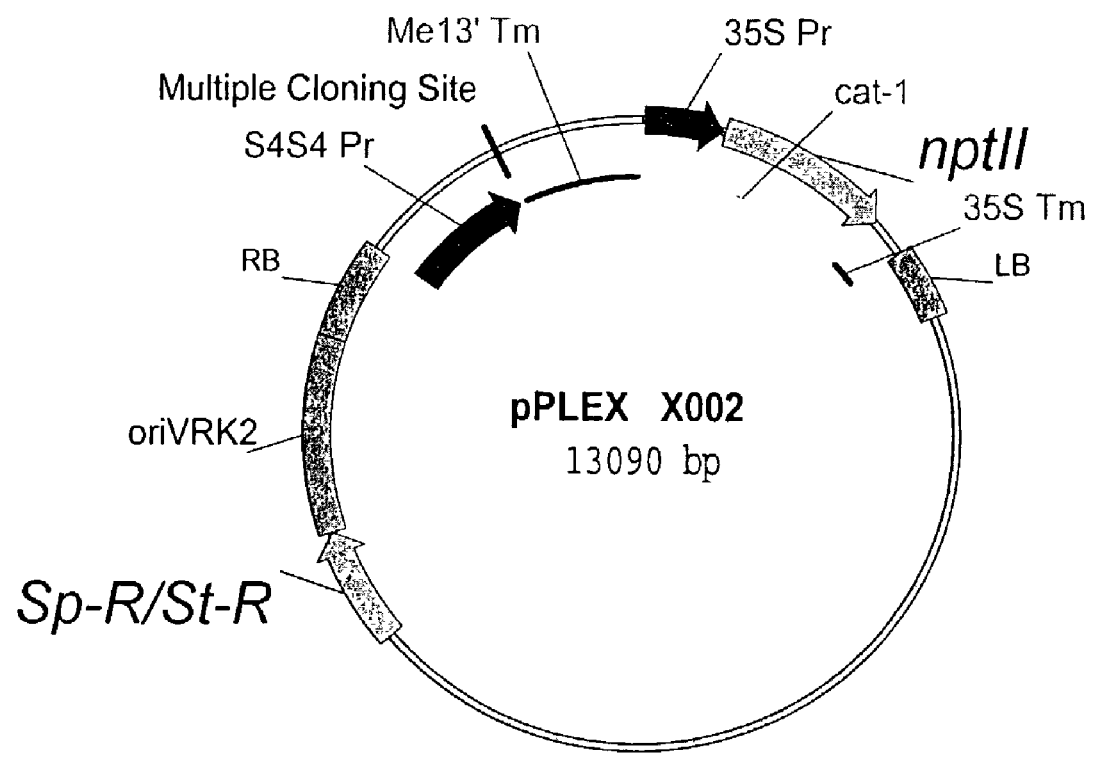

FIG. 12: The pPLEX X002 binary plasmid used in the transformation of SalAT 2 into poppy explants. The SalAT 2 cDNA was introduced into pPLEX X002 at the multiple cloning site between the S4S4 promoter and the Me1 terminator.

EXAMPLES

In the following Examples, salutaridinol 7-O-acetyltransferase [EC 2.3.1.150] has been characterized by purifying the native enzyme to apparent homogeneity, and determining amino acid sequences for internal peptides. A cDNA clone was then generated by RT-PCR using *P. somniferum* mRNA as template. Heterologous expression in a baculovirus vector in insect cells yielded functional enzyme that acetylated the 7-hydroxyl moiety of salutaridinol in the presence of acetyl CoA. Enzymic properties were determined for the recombinant protein. The apparent $K_m$ value for salutaridinol was determined to be 9 µM, and 54 µM for acetyl CoA.

An identical match was observed between the deduced (FIG. 8 (SEQ. ID No.14)) and directly determined amino acid sequences of ten internal peptides distributed throughout the open reading frame. The calculated molecular mass of the enzyme is 52.6 kDa, which is consistent with the apparent molecular mass of 50 kDa determined by SDS-PAGE (8). The amino acid sequence of salutaridinol 7-O-acetyltransferase is most similar (37% identity) to that of deacetylvindoline acetyltransferase of *Catharanthus roseus*

The results obtained by RACE-PCR indicated that the reading frame is 1425 nucleotides long corresponding to 474 amino acids (FIG. 10 (SEQ. ID No.15)). These values correlate well with the transcript size obtained by RNA gel blot analysis. The full length cDNA is illustrated in FIG. 9 (SEQ. ID No.13). Gene transcript was detected in extracts from *P. orientale* and *P. bracteatum*, in addition to *P. somniferum*. Genomic DNA gel blot analysis indicated that there is likely a single copy of this gene in the *P. somniferum* genome.

The abbreviations used are: RT-PCR, reverse transcriptase polymerase chain reaction; SDS-PAGE, sodium dodecyl sulfate polyacrylamide gel electrophoresis; HPLC, high performance liquid chromatography; RACE, rapid amplification of cDNA ends; HPLC-MS, high performance liquid chromatography mass spectrometry; SalAT, cDNA encoding salutaridinol 7-O-acetyltransferase; TLC, thin layer chromatography; CAPS, 3-(cyclohexylamino)-1-propanesulfonic acid; cor1, cDNA encoding codeinone reductase; cyp80b1, (S)-N-methylcoclaurine 3'-hydroxylase; DEPC, diethylpyrocarbonate I. Experimental Procedures Plant Material: Cultured suspension cells of opium poppy *Papaver somniferum* were provided by the cell culture laboratories of the Lehrstuhl für Pharmazeutische Biologie and of the Leibniz-Institut für Pflanzenbiochemie. Cultures were routinely grown in 1 liter conical flasks containing 400 ml of Linsmaier-Skoog medium (14) over 7 days at 23° C. on a gyratory shaker (100 rpm) in diffuse light (750 lux). Differentiated *P. somniferum, P. bracteatum, P. orientale, P. nudicaule, P. atlanticum, P. rhoeas* and *Chelidonium majus* plants were grown outdoors in Upper Bavaria or in Saxony-Anhalt. *P. somniferum* ssp. *setigerum* plants were grown in a greenhouse at 24° C., 18 h light and 50% humidity.

Purification of Native Enzyme and Amino Acid Sequence Analysis: Salutaridinol acetyltransferase was purified from *P. somniferum* cell suspension cultures exactly according to Lenz and Zenk (8). The purified enzyme preparation was subjected to SDS-PAGE to remove traces of impurities and the Coomassie brilliant blue R-250-visualized band representing the acetyltransferase was digested in situ with endoproteinase Lys-C as previously reported (15,16). The peptide mixture was resolved by reversed phase HPLC (column, Merck Lichrospher RP18; 5 µm (4×125 mm); solvent system (A) 0.1% trifluoroacetic acid (B) 0.1% trifluoroacetic acid/60% acetonitrile; gradient of 1% per min; flow rate of 1 ml min$^{-1}$) with detection at 206 nm. Microsequencing of ten of the peptides was accomplished on an Applied Biosystems model 470 gas-phase sequencer.

Generation of Partial cDNAs from *P. somniferum*: Partial cDNAs encoding salutaridinol acetyltransferase from *P. somniferum* were produced by PCR using cDNA generated by reverse transcription of mRNA isolated from 7-day-old suspension cultured cells. DNA amplification using either Taq or Pfu polymerase was performed under the following conditions: 3 min at 94° C., 35 cycles of 94° C., 30 s; 50° C., 30 s; 72° C., 1 min. At the end of 35 cycles, the reaction mixtures were incubated for an additional 7 min at 72° C. prior to cooling to 4° C. The amplified DNA was resolved by agarose gel electrophoresis, the bands of approximately correct size (537 bp) were isolated and subcloned into pGEM-T Easy (Promega) prior to nucleotide sequence determination. The specific sequences of the oligodeoxynucleotide primers used are given in the Results section.

Generation of Full-Length cDNAs: The sequence information requisite to the generation of a full-length cDNA was derived from the nucleotide sequence of the partial cDNA produced as described in the Results section. The complete nucleotide sequence was generated in two steps using one salutaridinol acetyltransferase-specific PCR primer (5'-GCC GCA GGC CAA CAA GGG TTG AGG TGG-3' (SEQ. ID No.2) for 5'-RACE and 5'-CCC ATC CTG CAC CAG CTA CTT ATC C-3' (SEQ. ID No.1) for 3'-RACE) and one RACE-specific primer as specified by the manufacturer. The 5'- and 3'-RACE-PCR experiments were carried out using a Marathon cDNA amplification kit (Clontech). RACE-PCR was performed using the following PCR cycle: 3 min at 94° C., 35 cycles of 94° C., 30 s; 60° C., 30 s; 72° C., 2 min. At the end of 35 cycles, the reaction mixtures were incubated for an additional 7 min at 72° C. prior to cooling to 4° C. The amplified DNA was resolved by agarose gel electrophoresis, the bands of the expected size (1265 bp for 5'-RACE and 917 bp for 3'-RACE) were isolated and subcloned into pGEM-T Easy prior to sequencing.

The full-length clone was generated in one piece using the primers 5'-CCA TGG CAA CAA TGT ATA GTG CTG CT-3' (SEQ. ID No.3) and 5'-AGA TCG AAT TCA ATA TCA AAT CAA TTC AAG G-3' (SEQ. ID No.4) for PCR with *P. somniferum* cell suspension culture cDNA as template. The final primers used for cDNA amplification contained recognition sites for the restriction endonucleases NcoI and EcoRI, appropriate for subcloning into pFastBac HTa (Life Technologies) for functional expression. DNA amplification was performed under the following conditions: 3 min at 94° C., 35 cycles of 94° C., 30 s; 60° C., 30 s; 72° C., 2 min. At the end of 35 cycles, the reaction mixtures were incubated for an additional 7 min at 72° C. prior to cooling to 4° C. The amplified DNA was resolved by agarose gel electrophoresis, the band of approximately correct size (1440 bp) was isolated and subcloned into pCR4-TOPO (Invitrogen) prior to nucleotide sequence determination.

Heterologous Expression and Enzyme Purification: The full-length cDNA generated by RT-PCR was ligated into pFastBac HTa that had been digested with restriction endonucleases NcoI and EcoRI. The recombinant plasmid was transposed into baculovirus DNA in the *Escherichia coli* strain DH10BAC (Life Technologies) and then transfected into *Spodoptera frugiperda* Sf9 cells according to the manufacturer'instructions. The insect cells were propagated and the recombinant virus was amplified according to (17, 18). INSECT-XPRESS serum-free medium (Bio Whittaker) was used in the enzyme expression experiments.

After infection of 150 ml suspension grown insect cells had proceeded for 3-4 days at 28° C. and 130 rpm, the cells were removed by centrifugation under sterile conditions at 1000×g for 10 min at 4° C. All subsequent steps were performed at 4° C. The pellet was discarded and the medium was slowly brought to 80% saturation with ammonium sulfate under constant slow stirring. The precipitated proteins were collected by centrifugation at 10,000×g for 30 min at 4° C. The pellet was dissolved in a minimal volume of 0.5 M NaCl, 10 mM beta-mercaptoethanol, 2.5 mM imidazole, 20 mM Tris-HCl adjusted finally to pH 7.0 and was dialyzed for 12-16 h against this same buffer. The His-tagged salutaridinol acetyltransferase was purified by affinity chromatography using a cobalt resin (Talon, Clontech) according to the manufacturer'instructions.

Enzyme Assay and Product Identification: The acetylation catalyzed by salutaridinol acetyltransferase was assayed according to Lenz and Zenk (8). The reaction mixture was extracted once with 1 volume $CHCl_3$ and was resolved by TLC (plates, silica gel 60 $F_{254}$, Merck; solvent system, chloroform:acetone:diethylamine (5:4:1)). The radioactivity present on the TLC plates was localized and quantitated with a Rita Star TLC scanner (Raytest). The identity of the enzymic reaction product as thebaine was ascertained by HPLC-MS using a Finnigan MAT TSQ 7000 (electrospray voltage 4.5 kV; capillary temperature 220° C.; carrier gas $N_2$) coupled to a Micro-Tech Ultra-Plus Micro-LC equipped with an Ultrasep RP18 column; 5 μm; 1×10 mm). Solvent system (A) 99.8% (v/v) $H_2O$, 0.2% HOAc (B) 99.8% $CH_3CN$ (v/v), 0.2% HOAc; gradient: 0-15 min 10-90% B, 15-25 min 90% B; flow 70 μl min$^{-1}$). The positive ion electrospray (ES) mass spectrum for thebaine (retention time 17.4±0.1 min; m/z=312) was characteristic of the standard reference compound.

General Methods: Latex was collected and resolved as previously described (19,20). Low molecular weight compounds were removed from the supernatant of the resolved latex by passage through a PD 10 column into 20 mM Tris, 10 mM-mercaptoethanol, pH 7.5 (Amersham Pharmacia). Total RNA was isolated and RNA gels were run and blotted as described previously (18). Genomic DNA was isolated and DNA gels were run and blotted according to (21). cDNA clones were labeled by PCR labeling with [alpha-$^{32}$P]dATP. Hybridized RNA on RNA gel blots and DNA on DNA gel blots were visualized with a STORM phosphor imager (Molecular Dynamics). The entire nucleotide sequence on both DNA strands of the full-length clone was determined by dideoxy cycle sequencing using internal DNA sequences for the design of deoxyoligonucleotides as sequencing primers. Saturation curves and double reciprocal plots were constructed with the FIG. P program Version 2.7 (Biosoft, Cambridge, UK). The influence of pH on enzyme activity was monitored in sodium citrate (pH 4-6), sodium phosphate (pH 6-7.5), Tris-HCl (pH 7.5-9), glycine/NaOH (pH 9-10.5) and CAPS (pH 10-12) buffered solutions.

II. Results

Purification and Amino Acid Sequence Analysis of Salutaridinol 7-O-Acetyltransferase-Salutaridinol 7-O-acetyltransferase was purified to apparent electrophoretic homogeneity from opium poppy cell suspension cultures and the amino acid sequence of ten endoproteinase Lys-C-generated peptides was determined. The sequences and relative positions of these internal peptides are indicated by unshaded boxes in FIG. 2 (SEQ. IDs Nos. 7 to 12). A comparison of these amino acid sequences with those available in the GenBank/EMBL sequence databases indicated no relevant similarity to known proteins. PCR primer pairs based on a series of salutaridinol 7-O-acetyltransferase peptide combinations also yielded only DNA fragments of irrelevant sequence.

Isolation of the cDNA Encoding Salutaridinol 7-O-Acetyltransferase: During the course of the initial RT-PCR experiments, sequence comparison information appeared in the literature for another acetyltransferase of plant alkaloid biosynthesis (22). The translation of the sequence of the cDNA encoding deacetylvindoline 4-O-acetyltransferase was homologous to a series of other putative plant acetyltransferases. A conserved region near the carboxy terminus of the proteins was used to design a degenerate antisense oligodeoxynucleotide primer for PCR. The sense primer was based upon an internal peptide sequence of salutaridinol 7-O-acetyltransferase. The primer sequences were as follows:

```
Sense Primer (FVFDFAK):
5' TTT/C GTG/A/T TTT/C GAC/T TTT/C GCA/T AA 3'        (SEQ. ID No.5)

Antisense Primer (DFGWG motif):
5' A/C/G/TGG C/TTT A/C/G/TCC CCA A/C/G/TCC G/AAA A/GTC 3'  (SEQ. ID No.6)
```

The positions of these peptides are indicated by arrows in FIG. 2 (SEQ. IDs Nos. 7 to 12). RT-PCR performed with this primer pair yielded a DNA product of the correct size and sequence for the opium poppy acetyltransferase. RACE-PCR was then used to generate each the 5'- and 3'-portions of the cDNA using nondegenerate nucleotide sequence information provided from the original PCR product.

Sequence Analysis of pSalAT: Translation of the complete nucleotide sequence of salAT yielded a polypeptide of 474 amino acids containing no apparent signal peptide. This is consistent with the cytosolic localization of the enzyme activity (6). The enzyme activity is also operationally found associated with the cytosolic fraction of exuded latex. The salAT amino acid sequence contains residues conserved in other plant acetyltransferases as indicated by the black boxes in FIG. 2 (SEQ. IDs No.7 to 12). The longest contiguous region of conserved amino acids are the five residues DFGWG near the carboxy terminus that were used for primer design and are indicated by an arrow. Conserved histidine and aspartate residues (HXXXD; denoted by # in FIG. 2) thought to be involved in catalysis as characterized by x-ray crystallography for the bacterial enzymes chloramphenicol acetyltransferase and dihydrolipoamide acetyltransferase are also present in salutaridinol 7-O-acetyltransferase (23,24). Covalent modification of salutaridinol 7-O-acetyltransferase by treatment with diethylpyrocarbonate (DEPC) resulted in the inhibition of enzyme activity (50% inhibition at 3 mM DEPC; 92% inhibition at 5 mM DEPC) (25). The inactivation by 5 mM DEPC could be reduced from 92% to 46% by preincubation of the enzyme with 30 mM acetyl CoA.

The amino acid sequence of salutaridinol 7-O-acetyltransferase is most similar (37% identity) to that of deacetylvindoline acetyltransferase of *C. roseus* (22). Other similar plant acyltransferases involved in secondary metabolism are benzylalcohol acetyltransferase from *Clarkia breweri* (34%) (26), anthranilate N-hydroxycinnamoyl/benzoyltransferase from *Dianthus caryophyllus* (25%) (27), taxadienol acetyltransferase (24%) and 10-deacetylbaccatin III-10-O-acetyltransferase (22%), both from *Taxus cuspidata* (28,29).

Genomic DNA and Gene Expression Analysis: A genomic DNA gel blot analysis of salAT in *P. somniferum* is presented in FIG. 3. The restriction endonucleases ApoI, SalI, SpeI and HincII each recognize one hydrolysis site within the salAT open reading frame, yielding two hybridizing bands on the Southern blot. There are no recognition sites for HindIII in the open reading frame. Correspondingly, only a single band hybridizes, but it is of approximately one half the predicted length. This indicates the possible presence of a small intron in the gene. Three recognition sites are present for MspI, theoretically resulting in four hybridizing DNA fragments. Two hybridizing bands of predictable length should have been present, one at 180 and 511 bp. The absence of these two bands also indicates that intron(s) may be present in the gene. No recognition site is present for EcoRI in the open reading frame, but two hybridizing bands are present on the gel blot, also suggesting an intron, which contains an EcoRI restriction site. A more thorough analysis of this point awaits isolation of a genomic clone. These results, taken together, support a single gene hypothesis, but do not exclude two very similar, clustered alleles.

This is in stark contrast to the other known morphine-specific biosynthetic gene cor1 encoding codeinone reductase, for which at least six alleles are expressed (13). RNA gel blot analysis suggests that, as for cor1, salAT is expressed in root, stem, leaf and capsule of the mature poppy plant (FIG. 4A) (12,13). There appears to be no organ-specific expression of either of these morphine biosynthetic genes. Analysis of RNA from several members of the genus *Papaver* demonstrates salAT transcript accumulation in three-week-old seedlings of *P. orientate* and *P. bracteatum*, though not in *P. atlanticum* or *P. nudicaule* (FIG. 4B). *P. orientate* accumulates the alternate biosynthetic precursor oripavine and *P. bracteatum* accumulates the morphine biosynthetic precursor thebaine, both of which structures contain the oxide bridge formed by action of salutaridinol 7-O-acetyltransferase. It was, therefore, expected that these two species should contain hybridizing salAT transcript. Neither *P. atlanticum* nor *P. nudicaule* contain an alkaloid with the morphinan skeleton, consistent with the absence of transcript in these two species.

Purification and Functional Characterization of Recombinant Enzyme: The salAT cDNA was constructed to express the recombinant protein with six histidine residues elongating the amino terminus. The protein was then purified from *Spodoptera frugiperda* Sf9 cell culture medium in two steps (ammonium sulfate precipitation/dialysis, cobalt affinity-chromatography) to yield electrophoretically homogeneous enzyme with an overall yield of 25% and 22-fold purification (FIG. 5). Per liter, the insect cell culture typically produced 2.0 mg (150 nmol s$^{-1}$) of recombinant enzyme.

Radioassay of pure, recombinant enzyme using [7-$^3$H] salutaridinol as substrate resulted in 100% conversion into a product that co-migrated during TLC with authentic thebaine standard (FIG. 6A-C). The positive ion electrospray mass spectrum of the enzymic product produced when salutaridinol was used as substrate correlated well with that of thebaine standard (FIG. 6D,E). The apparent $K_m$ value for salutaridinol was determined to be 9 μM at a fixed concentration of acetyl CoA of 30 mm. The apparent $K_m$ value for acetyl CoA was determined to be 54 μM at a fixed concentration of salutaridinol of 10 mM. The $V_{max}$ for the acetylation of salutaridinol was 25 pmol s$^{-1}$ with a temperature optimum of 47° C. and a pH optimal range of 7-9 under standard assay conditions. The recombinant enzyme acetylated 7(S)-salutaridinol and nudaurine (apparent $K_m$ nudaurine 23 μM at 30 mM acetyl CoA, apparent $K_m$ acetyl CoA 106 μM at 10 mM nudaurine, $V_{max}$ 19 pmol s$^{-1}$) at C-7, but not 7(R)-salutaridinol, salutaridine, codeine, morphine or deacetylvindoline. The kinetic values and chemical structures for the alkaloidal substrates salutaridinol and nudaurine are summarized in Table I. As designated by the ratio $k_{cat}/K_m$ (salutaridinol):$k_{cat}/K_m$ (nudaurine), the enzyme acetylates salutaridinol preferentially to nudaurine by a factor of 3.3.

Strain Deposit:

The cDNA encoding Salutaridinol 7-O-Acetyltransferase from *P. somniferum* (reading frame only, 1425 nucleotides as shown in FIG. 10 (SEQ. ID No.15)) has been deposited with the Deutsche Sammlung von Mikroorganismen und Zellkulturen GmbH (DSMZ) on 6$^{th}$ June 2002 under Accession number DSM 15044. The SalAT cDNA, carried in vector pCRT7/NT-TOPO in *E.coli* strain BL21DE3, is under the control of a T7 promoter. The plasmid further carries an ampicillin resistance gene.

Cloning of a Variant of SalAT 1 and its Transformation into Poppy.

The cDNA encoding SalAT 1 described above has enabled further SalAT sequences to be cloned from different *P. somniferum* lines. These results provide evidence of natural genetic variation.

A new cDNA was cloned from messenger RNA isolated from poppy cultivar CO48 (*Papaver somniferum*). Reverse transcriptase PCR using primers designed to the 5' and 3' UTR regions of the SalAT 1 sequence (FIG. 9 (SEQ. ID No.13)), amplified a product of the predicted size from CO48 which was cloned into pGEM-Teasy. The primers had the following sequences:

```
Forward primer: CCTCGAGCCA TTATCAATCC TGTTAAACAG TTAAACAC SAT_126F_XhoI    (SEQ. ID No.19)

Reverse primer: CCCTAGGGGA AATGGAGAAA ATCATGATTA CGGAACAC SAT_1639R_AvrII  (SEQ. ID No.18)
```

The primer SAT_126F_XhoI places a XhoI site on the end of the PCR product, and SAT_1639R_AvrII places an AvrII site on the end of the PCR product. This facilitates cloning first into pGEMT and then pPLEX.

Two independent RT PCR clones were sequenced. These two were identical to each other in sequence and are referred to as SAT2 CO48 (or SalAT 2). The SAT2 CO48 (SalAT 2) had an intact ATG for the start of translation and it differed from the original SalAT 1 clone in 6 nucleotides. The new CO48 cDNA (SalAT 2) sequence is illustrated in FIG. 11 (SEQ. ID No.17) and compared to the original clone. The two clones are in-frame throughout but there were 6 nucleotide differences resulting in 5 amino acid changes as shown.

The SAT2 CO48 (SalAT 2) cDNA was cloned into pPLEX X002 (FIG. 12) between the S4S4 promoter and the Me1 terminator. The S4S4 double promoter derives from subterranean clover stunt virus segment 4 (Boevink et al, 1995). The Me1 terminator derives from *Flaveria bidentis* malic enzyme gene (Marshall et al, 1997).

Clones were sequenced to verify sequence integrity. The transformation binary pPLEX X002-SAT was transformed into *Agrobacterium tumefaciens* strain Agl1 (Lazo et al, 1991). Sequencing verified the SalAT remained intact and unchanged after the transformation into Agrobacterium.

This was used to transform hypocotyl pieces of Tasmanian Alkaloids poppy cultivar CO58-34 (*P. somniferum*). The method used was as described in patent application "Methods for plant transformation and regeneration" [WO9934663]. Seedling hypocotyl pieces were incubated in a suspension of the Agrobacterium for 10-15 minutes. Explants were then transferred to medium B50medium consisting of B5 macronutrients, micronutrients, iron salts and vitamins (Gamborg et al, 1968), 20 $g.L^{-1}$ sucrose using 0.8% Agar, 1 $mg.L^{-1}$ 2,4-dichlorophenoxy acetic acid (2,4-D) and 10 mM MES buffer. The pH was adjusted with 1M KOH to pH 5.6.

After four to five days co-cultivation explants were washed in sterile distilled water, until the water was clear of evident Agrobacterial suspension, blotted on sterile filter paper and transferred to the same medium but contained 150 $mg.L^{-1}$ Timentin (to select against the Agrobacterium) and 25 $mg.L^{-1}$ paromomycin (to select for transformed plant cells). Explants were transferred to fresh medium of the same composition including antibiotic selection agents, every three weeks.

Explants initially produced transgenic translucent brownish callus consisting of large cells. This was termed type I callus. The transformed nature of the callus was demonstrated by growth on selective medium. Subsequently they formed small regions of white, compact embryogenic transgenic callus usually at about 7-8 weeks, and this was termed type II callus. Transgenic somatic embryos develop on this callus after 3-6 weeks and plantlets develop from these embryos and are transferred to soil.

REFERENCES

1. Novak, B. H., Hudlicky, T., Reed, J. W., Mulzer, J., and Trauner, D. (2000) *Current Organic Chemistry* 4, 343-362
2. Rice, K. C. (1980) *J. Org. Chem*. 45, 3135-3137
3. Kutchan, T. M. (1998) In *The Alkaloids*, Vol. 50 (Cordell, G., ed.) Academic Press, San Diego, pp.257-316
4. De-Eknamkul, W., and Zenk, M. H. (1992) *Phytochemistry* 31, 813-821
5. Gerardy, R., and Zenk, M. H. (1993) *Phytochemistry* 34, 125-132
6. Lenz, R., and Zenk, M. H. (1995) *Eur. J. Biochem*. 233, 132-139
7. Gerardy, R., and Zenk, M. H. (1993) *Phytochemistry* 32, 79-86
8. Lenz, R., and Zenk, M. H. (1995) *J. Biol. Chem*. 270, 31091-31096
9. Pfitzner, A., and Stöckigt, J. (1983) *Tetrahedron Lett*. 24, 5197-5200
10. Fahn, W., Gundlach, H., Deus-Neumann, B., and Stöckigt, J. (1985) *Plant Cell Rep*. 4, 333-336
11. De Luca, V., Balsevich, J., and Kurz, W. G. W. (1985) J. *Plant Physiol*. 121, 417-428
12. Huang, F.-C., and Kutchan, T. M. (2000) *Phytochemistry* 53, 555-564
13. Unterlinner, B., Lenz, R., and Kutchan, T. M. (1999) *Plant J*. 18, 465-475
14. Linsmaier, E. M., and Skoog, F. (1965) *Physiol. Plant*. 18, 100-127
15. Dittrich, H., and Kutchan, T. M. (1991) *Proc. Natl. Acad. Sci. USA* 88, 9969-9973
16. Eckerskorn, C., and Lottspeich, F. (1989) *Chromatographia* 28, 92-94
17. Kutchan, T. M., Bock, A., and Dittrich, H. (1994) *Phytochemistry* 35, 353-360
18. Pauli, H., and Kutchan, T. M. (1998) *Plant J*. 13, 793-801
19. Roberts, M. F., McCarthy, D., Kutchan, T. M., and Coscia, C. J. (1983) *Arch. Biochem. Biophys*. 222, 599-609
20. Decker G., Wanner G., Zenk M. H., and Lottspeich F. (2000) *Electrophoresis* 16, 3500-3516
21. Bracher, D., and Kutchan, T. M. (1992) *Arch. Biochem. Biophys*. 294, 717-723
22. St-Pierre, B., Laflamme, P., Alarco, A.-M., and De Luca, V. (1998) *Plant J*. 14, 703-713
23. Shaw, W. V., and Leslie, A. G. W. (1991) *Annu. Rev. Biophys. Biophys. Chem*. 20, 363-386
24. Hendle, J., Mattevi, A., Westphal, A. H., Spee, J., de Kok, A., Teplyakov, A., and Hol, W. G. (1995) *Biochemistry* 34, 4287-4298
25. Miles, E. W. (1977) *Methods Enzymol*. 47, 431-442
26. Dudareva, N., D'Auria, J. C., Nam, K. H., Raguso, R. A., and Pichersky, E. (1998) *Plant J*. 14, 297-304
27. Yang, Q., Reinhard, K., Schiltz, E., and Matern, U. (1997) *Plant Mol. Biol*. 35, 777-789
28. Walker, K., Schoendorf, A., and Croteau, R. (2000) *Arch. Biochem. Biophys*. 374, 371-380
29. Walker, K., and Croteau, R. (2000) *Proc. Natl. Acad. Sci. USA* 97, 583-587
30. Brown, N. F., Anderson, R. C., Caplan, S. L., Foster, D. W., and McGarry, J. D. (1994) *J. Biol. Chem*. 269, 19157-19162
31. Sinclair, J. C., Sandy, J., Delgoda, R., Sim, E., and Noble, M. E. M. (2000) *Nat. Struct. Biol*. 7, 560-564
32. Rush, M. D., Kutchan, T. M., and Coscia, C. J. (1985) *Plant Cell Rep*. 4, 237-240
33. Kutchan, T. M., Ayabe, S., and Coscia, C. J. (1985) In J. D. Phillipson, M. F. Roberts, M. H. Zenk, eds., The Chemistry and Biology of Isoquinoline Alkaloids, Springer-Verlag, Berlin, pp 281-294
34. Nessler, C. L., and Mahlberg, P. G. (1977) *Amer. J. Bot*. 64, 541-551
35. Nessler, C. L., and Mahlberg, P. G. (1978) *Amer. J. Bot*. 65, 978-983
36. St-Pierre, B., Vázquez-Flota, F. A., and De Luca, V. (1999) Plant Cell 11, 887-900
37. Frick, S., and Kutchan, T. M. (1999) Plant J. 17, 329-339
38. Rosco, A., Pauli, H. H., Priesner, W., and Kutchan, T. M. (1997) Arch. Biochem. Biophys. 348, 369-377
39. Wieczorek, U. Dissertation der Fakulät für Chemie und Pharmazie der Ludwig-Maximiliens-Universität zu München: „Entwicklung radioimmunologischer Methoden zur Bestimmung von Opiumalkaloiden in *Papaver*-Pflanzen und -Zellkulturen" 1985.
40. Hauschild K., Pauli H. H., Kutchan T. M. (1998) Plant Molecular Biology, 36, 473-478
41. Park S. U., Johnson A. G., Penzes-Yost, C., Facchini P. J., Plant Molecular Biology, (1999) 40, 121-131
42. Belny M., Hérouart D., Thomasset B., David H., Jacquin-Dubreuil A., David A. (1997) Physiologia Plantarum 99 233-240
43. Elleuch H. et al., Enzyme Microb Technol (2001) 29 (1) 106-113
44. Yoshimatsu K, Shimomura K (1992) Plant Cell Reports 11, 132-136
45. Park S. U., Facchini P. J., (2000) J. Exp. Botany, 51 (347) 1005-1016
46. Lazo, G. R., Stein, P. A. and Ludwig, R. A. (1991) A DNA transformation-competent Arabidopsis genomic library in Agrobacterium. Bio/Technology, 9, 963-967.
47. Boevink P., Chu P. W. G., and Keese P. (1995). Sequence of subterranean clover stunt virus DNA: affinities with the geminiviruses. Virology (New York) 207:354-361.
48. Marshall J. S., Stubbs J. D., Chitty J. A., Surin B., and Taylor W. C. (1997). Expression of the C4 Me1 gene from Flaveria bidentis requires an interaction between 5' and 3' sequences. Plant Cell 9:1515-1525.
49. Gamborg, O. L., Miller, R. A. and Ojima, K. (1968). Nutrient requirements of suspension cultures of soybean root cells. Exp. Cells Res. 50, 151-158.

What is claimed is:

1. An isolated nucleic acid comprising the coding sequence of the molecule SAT 2 CO48 illustrated in FIG. 11 (SEQ. ID No. 17).

2. An isolated nucleic acid encoding a protein comprising consecutive amino acids, the amino acid sequence of which comprises the amino acid sequence illustrated in FIG. 8 (SEQ. ID No. 14).

3. An isolated nucleic acid comprising consecutive nucleotides, the nucleotide sequence of which comprises the nucleic acid sequence illustrated in FIG. 9 (SEQ. ID No. 13) or FIG. 10 (SEQ. ID No. 15).

4. A method for producing a protein having salutaridinol 7-O-acetyltransferase activity, said method comprising i) transforming or transfecting a cell with a nucleic acid according to claim 1, under conditions permitting the expression of the protein having salutaridinol 7-O-acetyltransferase activity, ii) propagating said cells, and iii) recovering the thus-produced protein having salutaridinol 7-O-acetyltransferase activity.

5. A method for producing a protein having salutaridinol 7-O-acetyltransferase activity, said method comprising i) transforming or transfecting a cell with a nucleic acid according to claim 2, under conditions permitting the expression of the protein having salutaridinol 7-O-acetyltransferase activity, ii) propagating said cells, and iii) recovering the thus-produced protein having salutaridinol 7-O-acetyltransferase activity.

6. A method for producing a protein having salutaridinol 7-O-acetyltransferase activity, said method comprising i) transforming or transfecting a cell with a nucleic acid according to claim 3, under conditions permitting the expression of the protein having salutaridinol 7-O-acetyltransferase activity, ii) propagating said cells, and iii) recovering the thus-produced protein having salutaridinol 7-O-acetyltransferase activity.

* * * * *

SEQUENCE LISTING

```
<160> NUMBER OF SEQ ID NOS: 19

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Xho I
      primer

<400> SEQUENCE: 1
cccatcctgc accagctact tatc                                          24

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 2
gccgcaggcc aacaagggtt gaggtgg                                       27

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 3
ccatggcaac aatgtatagt gctgct                                        26

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: PCR primer

<400> SEQUENCE: 4
agatcgaatt caatatcaaa tcaattcaag g                                  31

<210> SEQ ID NO 5
<211> LENGTH: 20
<212> TYPE: DNA
<213> ORGANISM: Artificial Sequence
```

```
<220> FEATURE:
<223> OTHER INFORMATION: Description of Artificial Sequence: sense
      primer

<400> SEQUENCE: 5
ttygtdttyg ayttygcwaa                                                        20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: antisense
      primer
<220> FEATURE:
<221> NAME/KEY: misc_feature
<222> LOCATION: 1...1
<223> OTHER INFORMATION: n is any of a, c, g, or t
<220> FEATURE:
<221> NAME/KEY: misc_feature
<222> LOCATION: 7...7
<223> OTHER INFORMATION: n is any of a, c, g, or t
<220> FEATURE:
<221> NAME/KEY: misc_feature
<222> LOCATION: 13...13
<223> OTHER INFORMATION: n is any of a, c, g, or t

<400> SEQUENCE: 6
nggyttnccc canccraart c                                                      21

<210> SEQ ID NO 7
<211> LENGTH: 474
<212> TYPE: PRT
<213> ORGANISM: Papaver somniferum

<400> SEQUENCE: 7

Met Ala Thr Met Tyr Ser Ala Ala Val Glu Val Ile Ser Lys Glu Thr
  1               5                  10                  15

Ile Lys Pro Thr Thr Pro Thr Pro Ser Gln Leu Lys Asn Phe Asn Leu
             20                  25                  30

Ser Leu Leu Asp Gln Cys Phe Pro Leu Tyr Tyr Tyr Val Pro Ile Ile
         35                  40                  45

Leu Phe Tyr Pro Ala Thr Ala Ala Asn Ser Thr Gly Ser Ser Asn His
     50                  55                  60

His Asp Asp Leu Asp Leu Leu Lys Ser Ser Leu Ser Lys Thr Leu Val
 65                  70                  75                  80

His Phe Tyr Pro Met Ala Gly Arg Met Ile Asp Asn Ile Leu Val Asp
                 85                  90                  95

Cys His Asp Gln Gly Ile Asn Phe Tyr Lys Val Lys Ile Arg Gly Lys
            100                 105                 110

Met Cys Glu Phe Met Ser Gln Pro Asp Val Pro Leu Ser Gln Leu Leu
        115                 120                 125

Pro Ser Glu Val Val Ser Ala Ser Val Pro Lys Glu Ala Leu Val Ile
    130                 135                 140

Val Gln Val Asn Met Phe Asp Cys Gly Gly Thr Ala Ile Cys Ser Ser
145                 150                 155                 160

Val Ser His Lys Ile Ala Asp Ala Ala Thr Met Ser Thr Phe Ile Arg
                165                 170                 175

Ser Trp Ala Ser Thr Thr Lys Thr Ser Arg Ser Gly Gly Ser Thr Ala
            180                 185                 190

Ala Val Thr Asp Gln Lys Leu Ile Pro Ser Phe Asp Ser Ala Ser Leu
        195                 200                 205
```

```
Phe Pro Pro Ser Glu Arg Leu Thr Ser Pro Ser Gly Met Ser Glu Ile
    210                 215                 220

Pro Phe Ser Ser Thr Pro Glu Asp Thr Glu Asp Asp Lys Thr Val Ser
225                 230                 235                 240

Lys Arg Phe Val Phe Asp Phe Ala Lys Ile Thr Ser Val Arg Glu Lys
                245                 250                 255

Leu Gln Val Leu Met His Asp Asn Tyr Lys Ser Arg Arg Gln Thr Arg
            260                 265                 270

Val Glu Val Val Thr Ser Leu Ile Trp Lys Ser Val Met Lys Ser Thr
            275                 280                 285

Pro Ala Gly Phe Leu Pro Val His His Ala Val Asn Leu Arg Lys
    290                 295                 300

Lys Met Asp Pro Pro Leu Gln Asp Val Ser Phe Gly Asn Leu Ser Val
305                 310                 315                 320

Thr Val Ser Ala Phe Leu Pro Ala Thr Thr Thr Thr Thr Asn Ala
                325                 330                 335

Val Asn Lys Thr Ile Asn Ser Thr Ser Ser Glu Ser Gln Val Val Leu
            340                 345                 350

His Glu Leu His Asp Phe Ile Ala Gln Met Arg Ser Glu Ile Asp Lys
            355                 360                 365

Val Lys Gly Asp Lys Gly Ser Leu Glu Lys Val Ile Gln Asn Phe Ala
    370                 375                 380

Ser Gly His Asp Ala Ser Ile Lys Lys Ile Asn Asp Val Glu Val Ile
385                 390                 395                 400

Asn Phe Trp Ile Ser Ser Trp Cys Arg Met Gly Leu Tyr Glu Ile Asp
                405                 410                 415

Phe Gly Trp Gly Lys Pro Ile Trp Val Thr Val Asp Pro Asn Ile Lys
            420                 425                 430

Pro Asn Lys Asn Cys Phe Phe Met Asn Asp Thr Lys Cys Gly Glu Gly
        435                 440                 445

Ile Glu Val Trp Ala Ser Phe Leu Glu Asp Asp Met Ala Lys Phe Glu
    450                 455                 460

Leu His Leu Ser Glu Ile Leu Glu Leu Ile
465                 470

<210> SEQ ID NO 8
<211> LENGTH: 439
<212> TYPE: PRT
<213> ORGANISM: C. roseus

<400> SEQUENCE: 8

Met Glu Ser Gly Lys Ile Ser Val Glu Thr Glu Thr Leu Ser Lys Thr
1               5                   10                  15

Leu Ile Lys Pro Ser Pro Thr Pro Gln Ser Leu Ser Arg Tyr Asn
            20                  25                  30

Leu Ser Tyr Asn Asp Gln Asn Ile Tyr Gln Thr Cys Val Ser Val Gly
        35                  40                  45

Phe Phe Tyr Glu Asn Pro Asp Gly Ile Glu Ile Ser Thr Ile Arg Glu
    50                  55                  60

Gln Leu Gln Asn Ser Leu Ser Lys Thr Leu Val Ser Tyr Tyr Pro Phe
65                  70                  75                  80

Ala Gly Lys Val Val Lys Asn Asp Tyr Ile His Cys Asn Asp Asp Gly
                85                  90                  95

Ile Glu Phe Val Glu Val Arg Ile Arg Cys Arg Met Asn Asp Ile Leu
                100                 105                 110
```

```
Lys Tyr Glu Leu Arg Ser Tyr Ala Arg Asp Leu Val Leu Pro Lys Arg
        115                 120                 125

Val Thr Val Gly Ser Glu Asp Thr Thr Ala Ile Val Gln Leu Ser His
    130                 135                 140

Phe Asp Cys Gly Gly Leu Ala Val Ala Phe Gly Ile Ser His Lys Val
145                 150                 155                 160

Ala Asp Gly Gly Thr Ile Ala Ser Phe Met Lys Asp Trp Ala Ala Ser
                165                 170                 175

Ala Cys Tyr Leu Ser Ser Ser His His Val Pro Thr Pro Leu Leu Val
            180                 185                 190

Ser Asp Ser Ile Phe Pro Arg Gln Asp Asn Ile Ile Cys Glu Gln Phe
        195                 200                 205

Pro Thr Ser Lys Asn Cys Val Glu Lys Thr Phe Ile Phe Pro Pro Glu
    210                 215                 220

Ala Ile Glu Lys Leu Lys Ser Lys Ala Val Glu Phe Gly Ile Glu Lys
225                 230                 235                 240

Pro Thr Arg Val Glu Val Leu Thr Ala Phe Leu Ser Arg Cys Ala Thr
                245                 250                 255

Val Ala Gly Lys Ser Ala Ala Lys Asn Asn Cys Gly Gln Ser Leu
            260                 265                 270

Pro Phe Pro Val Leu Gln Ala Ile Asn Leu Arg Pro Ile Leu Glu Leu
        275                 280                 285

Pro Gln Asn Ser Val Gly Asn Leu Val Ser Ile Tyr Phe Ser Arg Thr
    290                 295                 300

Ile Lys Glu Asn Asp Tyr Leu Asn Glu Lys Glu Tyr Thr Lys Leu Val
305                 310                 315                 320

Ile Asn Glu Leu Arg Lys Glu Lys Gln Lys Ile Lys Asn Leu Ser Arg
                325                 330                 335

Glu Lys Leu Thr Tyr Val Ala Gln Met Glu Glu Phe Val Lys Ser Leu
            340                 345                 350

Lys Glu Phe Asp Ile Ser Asn Phe Leu Asp Ile Asp Ala Tyr Leu Ser
        355                 360                 365

Asp Ser Trp Cys Arg Phe Pro Phe Tyr Asp Val Asp Phe Gly Trp Gly
    370                 375                 380

Lys Pro Ile Trp Val Cys Leu Phe Gln Pro Tyr Ile Lys Asn Cys Val
385                 390                 395                 400

Val Met Met Asp Tyr Pro Phe Gly Asp Asp Tyr Gly Ile Glu Ala Ile
                405                 410                 415

Val Ser Phe Glu Gln Glu Lys Met Ser Ala Phe Glu Lys Asn Glu Gln
            420                 425                 430

Leu Leu Gln Phe Val Ser Asn
        435

<210> SEQ ID NO 9
<211> LENGTH: 433
<212> TYPE: PRT
<213> ORGANISM: Clarkia breweri

<400> SEQUENCE: 9

Met Asn Val Thr Met His Ser Lys Lys Leu Leu Lys Pro Ser Ile Pro
1               5                   10                  15

Thr Pro Asn His Leu Gln Lys Leu Asn Leu Ser Leu Leu Asp Gln Ile
            20                  25                  30

Gln Ile Pro Phe Tyr Val Gly Leu Ile Phe His Tyr Glu Thr Leu Ser
        35                  40                  45
```

-continued

```
Asp Asn Ser Asp Ile Thr Leu Ser Lys Leu Glu Ser Ser Leu Ser Glu
     50                  55                  60

Thr Leu Thr Leu Tyr Tyr His Val Ala Gly Arg Tyr Asn Gly Thr Asp
 65                  70                  75                  80

Cys Val Ile Glu Cys Asn Asp Gln Gly Ile Gly Tyr Val Glu Thr Ala
                 85                  90                  95

Phe Asp Val Glu Leu His Gln Phe Leu Leu Gly Glu Glu Ser Asn Asn
            100                 105                 110

Leu Asp Leu Leu Val Gly Leu Ser Gly Phe Leu Ser Glu Thr Glu Thr
        115                 120                 125

Pro Pro Leu Ala Ala Ile Gln Leu Asn Met Phe Lys Cys Gly Gly Leu
    130                 135                 140

Val Ile Gly Ala Gln Phe Asn His Ile Ile Gly Asp Met Phe Thr Met
145                 150                 155                 160

Ser Thr Phe Met Asn Ser Trp Ala Lys Ala Cys Arg Val Gly Ile Lys
                165                 170                 175

Glu Val Ala His Pro Thr Phe Gly Leu Ala Pro Leu Met Pro Ser Ala
            180                 185                 190

Lys Val Leu Asn Ile Pro Pro Pro Pro Ser Phe Glu Gly Val Lys Phe
        195                 200                 205

Val Ser Lys Arg Phe Val Phe Asn Glu Asn Ala Ile Thr Arg Leu Arg
    210                 215                 220

Lys Glu Ala Thr Glu Glu Asp Gly Asp Gly Asp Asp Asp Gln Lys Lys
225                 230                 235                 240

Lys Arg Pro Ser Arg Val Asp Leu Val Thr Ala Phe Leu Ser Lys Ser
                245                 250                 255

Leu Ile Glu Met Asp Cys Ala Lys Lys Glu Gln Thr Lys Ser Arg Pro
            260                 265                 270

Ser Leu Met Val His Met Met Asn Leu Arg Lys Arg Thr Lys Leu Ala
        275                 280                 285

Leu Glu Asn Asp Val Ser Gly Asn Phe Phe Ile Val Val Asn Ala Glu
    290                 295                 300

Ser Lys Ile Thr Val Ala Pro Lys Ile Thr Asp Leu Thr Glu Ser Leu
305                 310                 315                 320

Gly Ser Ala Cys Gly Glu Ile Ile Ser Glu Val Ala Lys Val Asp Asp
                325                 330                 335

Ala Glu Val Val Ser Ser Met Val Leu Asn Ser Val Arg Glu Phe Tyr
            340                 345                 350

Tyr Glu Trp Gly Lys Gly Glu Lys Asn Val Phe Leu Tyr Thr Ser Trp
        355                 360                 365

Cys Arg Phe Pro Leu Tyr Glu Val Asp Phe Gly Trp Gly Ile Pro Ser
    370                 375                 380

Leu Val Asp Thr Thr Ala Val Pro Phe Gly Leu Ile Val Leu Met Asp
385                 390                 395                 400

Glu Ala Pro Ala Gly Asp Gly Ile Ala Val Arg Ala Cys Leu Ser Glu
                405                 410                 415

His Asp Met Ile Gln Phe Gln Gln His His Gln Leu Leu Ser Tyr Val
            420                 425                 430

Ser

<210> SEQ ID NO 10
<211> LENGTH: 445
<212> TYPE: PRT
<213> ORGANISM: Dianthus caryophyllus
```

```
<400> SEQUENCE: 10

Met Ser Ile Gln Ile Lys Gln Ser Thr Met Val Arg Pro Ala Glu Glu
 1               5                  10                  15

Thr Pro Asn Lys Ser Leu Trp Leu Ser Asn Ile Asp Met Ile Leu Arg
             20                  25                  30

Thr Pro Tyr Ser His Thr Gly Ala Val Leu Ile Tyr Lys Gln Pro Asp
         35                  40                  45

Asn Asn Glu Asp Asn Ile His Pro Ser Ser Met Tyr Phe Asp Ala
     50                  55                  60

Asn Ile Leu Ile Glu Ala Leu Ser Lys Ala Leu Val Pro Phe Tyr Pro
 65                  70                  75                  80

Met Ala Gly Arg Leu Lys Ile Asn Gly Asp Arg Tyr Glu Ile Asp Cys
                 85                  90                  95

Asn Ala Glu Gly Ala Leu Phe Val Glu Ala Glu Ser Ser His Val Leu
             100                 105                 110

Glu Asp Phe Gly Asp Phe Arg Pro Asn Asp Glu Leu His Arg Val Met
         115                 120                 125

Val Pro Thr Cys Asp Tyr Ser Lys Gly Ile Ser Ser Phe Pro Leu Leu
     130                 135                 140

Met Val Gln Leu Thr Arg Phe Arg Cys Gly Gly Val Ser Ile Gly Phe
145                 150                 155                 160

Ala Gln His His His Val Cys Asp Gly Met Ala His Phe Glu Phe Asn
                 165                 170                 175

Asn Ser Trp Ala Arg Ile Ala Lys Gly Leu Leu Pro Ala Leu Glu Pro
             180                 185                 190

Val His Asp Arg Tyr Leu His Leu Arg Pro Arg Asn Pro Pro Gln Ile
         195                 200                 205

Lys Tyr Ser His Ser Gln Phe Glu Pro Phe Val Pro Ser Leu Pro Asn
     210                 215                 220

Glu Leu Leu Asp Gly Lys Thr Asn Lys Ser Gln Thr Leu Phe Ile Leu
225                 230                 235                 240

Ser Arg Glu Gln Ile Asn Thr Leu Lys Gln Lys Leu Asp Leu Ser Asn
                 245                 250                 255

Asn Thr Thr Arg Leu Ser Thr Tyr Glu Val Val Ala Ala His Val Trp
             260                 265                 270

Arg Ser Val Ser Lys Ala Arg Gly Leu Ser Asp His Glu Glu Ile Lys
         275                 280                 285

Leu Ile Met Pro Val Asp Gly Arg Ser Arg Ile Asn Asn Pro Ser Leu
     290                 295                 300

Pro Lys Gly Tyr Cys Gly Asn Val Val Phe Leu Ala Val Cys Thr Ala
305                 310                 315                 320

Thr Val Gly Asp Leu Ser Cys Asn Pro Leu Thr Asp Thr Ala Gly Lys
                 325                 330                 335

Val Gln Glu Ala Leu Lys Gly Leu Asp Asp Tyr Leu Arg Ser Ala
             340                 345                 350

Ile Asp His Thr Glu Ser Lys Pro Gly Leu Pro Val Pro Tyr Met Gly
         355                 360                 365

Ser Pro Glu Lys Thr Leu Tyr Pro Asn Val Leu Val Asn Ser Trp Gly
     370                 375                 380

Arg Ile Pro Tyr Gln Ala Met Asp Phe Gly Trp Gly Ser Pro Thr Phe
385                 390                 395                 400

Phe Gly Ile Ser Asn Ile Phe Tyr Asp Gly Gln Cys Phe Leu Ile Pro
                 405                 410                 415
```

Ser Arg Asp Gly Asp Gly Ser Met Thr Leu Ala Ile Asn Leu Phe Ser
            420                 425                 430

Ser His Leu Ser Arg Phe Lys Lys Tyr Phe Tyr Asp Phe
        435                 440                 445

<210> SEQ ID NO 11
<211> LENGTH: 440
<212> TYPE: PRT
<213> ORGANISM: Taxus cuspidata

<400> SEQUENCE: 11

Met Ala Gly Ser Thr Glu Phe Val Val Arg Ser Leu Glu Arg Val Met
 1               5                  10                  15

Val Ala Pro Ser Gln Pro Ser Pro Lys Ala Phe Leu Gln Leu Ser Thr
            20                  25                  30

Leu Asp Asn Leu Pro Gly Val Arg Glu Asn Ile Phe Asn Thr Leu Leu
        35                  40                  45

Val Tyr Asn Ala Ser Asp Arg Val Ser Val Asp Pro Ala Lys Val Ile
    50                  55                  60

Arg Gln Ala Leu Ser Lys Val Leu Val Tyr Tyr Ser Pro Phe Ala Gly
 65                  70                  75                  80

Arg Leu Arg Lys Lys Glu Asn Gly Asp Leu Glu Val Glu Cys Thr Gly
                85                  90                  95

Glu Gly Ala Leu Phe Val Glu Ala Met Ala Asp Thr Asp Leu Ser Val
            100                 105                 110

Leu Gly Asp Leu Asp Asp Tyr Ser Pro Ser Leu Glu Gln Leu Leu Phe
        115                 120                 125

Cys Leu Pro Pro Asp Thr Asp Ile Glu Asp Ile His Pro Leu Val Val
    130                 135                 140

Gln Val Thr Arg Phe Thr Cys Gly Gly Phe Val Val Gly Val Ser Phe
145                 150                 155                 160

Cys His Gly Ile Cys Asp Gly Leu Gly Ala Gly Gln Phe Leu Ile Ala
                165                 170                 175

Met Gly Glu Met Ala Arg Gly Glu Ile Lys Pro Ser Ser Glu Pro Ile
            180                 185                 190

Trp Lys Arg Glu Leu Leu Lys Pro Glu Asp Pro Leu Tyr Arg Phe Gln
        195                 200                 205

Tyr Tyr His Phe Gln Leu Ile Cys Pro Pro Ser Thr Phe Gly Lys Ile
    210                 215                 220

Val Gln Gly Ser Leu Val Ile Thr Ser Glu Thr Ile Asn Cys Ile Lys
225                 230                 235                 240

Gln Cys Leu Arg Glu Glu Ser Lys Glu Phe Cys Ser Ala Phe Glu Val
                245                 250                 255

Val Ser Ala Leu Ala Trp Ile Ala Arg Thr Arg Ala Leu Gln Ile Pro
            260                 265                 270

His Ser Glu Asn Val Lys Leu Ile Phe Ala Met Asp Met Arg Lys Leu
        275                 280                 285

Phe Asn Pro Pro Leu Ser Lys Gly Tyr Tyr Gly Asn Phe Val Gly Thr
    290                 295                 300

Val Cys Ala Met Asp Asn Val Lys Asp Leu Leu Ser Gly Ser Leu Leu
305                 310                 315                 320

Arg Val Val Arg Ile Ile Lys Lys Ala Lys Val Ser Leu Asn Glu His
                325                 330                 335

Phe Thr Ser Thr Ile Val Thr Pro Arg Ser Gly Ser Asp Glu Ser Ile
            340                 345                 350

```
Asn Tyr Glu Asn Ile Val Gly Phe Gly Asp Arg Arg Leu Gly Phe
            355                 360                 365

Asp Glu Val Asp Phe Gly Trp Gly His Ala Asp Asn Val Ser Leu Val
370                 375                 380

Gln His Gly Leu Lys Asp Val Ser Val Val Gln Ser Tyr Phe Leu Phe
385                 390                 395                 400

Ile Arg Pro Pro Lys Asn Asn Pro Asp Gly Ile Lys Ile Leu Ser Phe
            405                 410                 415

Met Pro Pro Ser Ile Val Lys Ser Phe Lys Phe Glu Met Glu Thr Met
            420                 425                 430

Thr Asn Lys Tyr Val Thr Lys Pro
            435                 440

<210> SEQ ID NO 12
<211> LENGTH: 439
<212> TYPE: PRT
<213> ORGANISM: Taxus cuspidata

<400> SEQUENCE: 12

Met Glu Lys Thr Asp Leu His Val Asn Leu Ile Glu Lys Val Met Val
1               5                   10                  15

Gly Pro Ser Pro Leu Pro Lys Thr Thr Leu Gln Leu Ser Ser Ile
            20                  25                  30

Asp Asn Leu Pro Gly Val Arg Gly Ser Ile Phe Asn Ala Leu Leu Ile
            35                  40                  45

Tyr Asn Ala Ser Pro Ser Pro Thr Met Ile Ser Ala Asp Pro Ala Lys
        50                  55                  60

Pro Ile Arg Glu Ala Leu Ala Lys Ile Leu Val Tyr Tyr Pro Pro Phe
65                  70                  75                  80

Ala Gly Arg Leu Arg Glu Thr Glu Asn Gly Asp Leu Glu Val Glu Cys
                85                  90                  95

Thr Gly Glu Gly Ala Met Phe Leu Glu Ala Met Ala Asp Asn Glu Leu
                100                 105                 110

Ser Val Leu Gly Asp Phe Asp Asp Ser Asn Pro Ser Phe Gln Gln Leu
        115                 120                 125

Leu Phe Ser Leu Pro Leu Asp Thr Asn Phe Lys Asp Leu Ser Leu Leu
130                 135                 140

Val Val Gln Val Thr Arg Phe Thr Cys Gly Gly Phe Val Val Gly Val
145                 150                 155                 160

Ser Phe His His Gly Val Cys Asp Gly Arg Gly Ala Ala Gln Phe Leu
                165                 170                 175

Lys Gly Leu Ala Glu Met Ala Arg Gly Glu Val Lys Leu Ser Leu Glu
            180                 185                 190

Pro Ile Trp Asn Arg Glu Leu Val Lys Leu Asp Asp Pro Lys Tyr Leu
        195                 200                 205

Gln Phe Phe His Phe Glu Phe Leu Arg Ala Pro Ser Ile Val Glu Lys
    210                 215                 220

Ile Val Gln Thr Tyr Phe Ile Ile Asp Phe Glu Thr Ile Asn Tyr Ile
225                 230                 235                 240

Lys Gln Ser Val Met Glu Glu Cys Lys Glu Phe Cys Ser Ser Phe Glu
                245                 250                 255

Val Ala Ser Ala Met Thr Trp Ile Ala Arg Thr Arg Ala Phe Gln Ile
            260                 265                 270

Pro Glu Ser Glu Tyr Val Lys Ile Leu Phe Gly Met Asp Met Arg Asn
        275                 280                 285
```

```
Ser Phe Asn Pro Pro Leu Pro Ser Gly Tyr Tyr Gly Asn Ser Ile Gly
    290                 295                 300

Thr Ala Cys Ala Val Asp Asn Val Gln Asp Leu Leu Ser Gly Ser Leu
305                 310                 315                 320

Leu Arg Ala Ile Met Ile Ile Lys Lys Ser Lys Val Ser Leu Asn Asp
                325                 330                 335

Asn Phe Lys Ser Arg Ala Val Val Lys Pro Ser Glu Leu Asp Val Asn
            340                 345                 350

Met Asn His Glu Asn Val Val Ala Phe Ala Asp Trp Ser Arg Leu Gly
        355                 360                 365

Phe Asp Glu Val Asp Phe Gly Trp Gly Asn Ala Val Ser Val Ser Pro
370                 375                 380

Val Gln Gln Gln Ser Ala Leu Ala Met Gln Asn Tyr Phe Leu Phe Leu
385                 390                 395                 400

Lys Pro Ser Lys Asn Lys Pro Asp Gly Ile Lys Ile Leu Met Phe Leu
                405                 410                 415

Pro Leu Ser Lys Met Lys Ser Phe Lys Ile Glu Met Glu Ala Met Met
            420                 425                 430

Lys Lys Tyr Val Ala Lys Val
            435

<210> SEQ ID NO 13
<211> LENGTH: 1785
<212> TYPE: DNA
<213> ORGANISM: Papaver somniferum
<220> FEATURE:
<221> NAME/KEY: CDS
<222> LOCATION: (166)..(1587)

<400> SEQUENCE: 13
gagagtttct tcttatccag ctcctcgcaa atgaaatgat tccataatac ctctctaaaa      60
gacttggtca ttatataaga gagggagacc acgagcttct tctaaacaac agaaagtatc     120
atctaccatt atcaatcctg ttaaacagtt aaacactttg gatat atg gca aca atg     177
                                                 Met Ala Thr Met
                                                   1 tat agt gct gct gtt gaa gtg atc tct aag gaa acc att aaa ccc aca       225
Tyr Ser Ala Ala Val Glu Val Ile Ser Lys Glu Thr Ile Lys Pro Thr
  5                  10                  15                  20 act cca acc cca tct caa ctt aaa aac ttc aat ctg tca ctt ctc gat       273
Thr Pro Thr Pro Ser Gln Leu Lys Asn Phe Asn Leu Ser Leu Leu Asp
                 25                  30                  35 caa tgt ttt cct tta tat tat tat gtt cca atc att ctt ttc tac cca       321
Gln Cys Phe Pro Leu Tyr Tyr Tyr Val Pro Ile Ile Leu Phe Tyr Pro
             40                  45                  50 gcc acc gcc gct aat agt acc ggt agc agt aac cat cat gat gat ctt       369
Ala Thr Ala Ala Asn Ser Thr Gly Ser Ser Asn His His Asp Asp Leu
         55                  60                  65 gac ttg ctt aag agt tct ctt tcc aaa aca cta gtt cac ttt tat cca       417
Asp Leu Leu Lys Ser Ser Leu Ser Lys Thr Leu Val His Phe Tyr Pro
 70                  75                  80 atg gct ggt agg atg ata gac aat att ctg gtc gac tgt cat gac caa       465
Met Ala Gly Arg Met Ile Asp Asn Ile Leu Val Asp Cys His Asp Gln
 85                  90                  95                 100 ggg att aac ttt tac aaa gtt aaa att aga ggt aaa atg tgt gag ttc       513
Gly Ile Asn Phe Tyr Lys Val Lys Ile Arg Gly Lys Met Cys Glu Phe
                105                 110                 115
```

| | |
|---|---|
| atg tcg caa ccg gat gtg cca cta agc cag ctt ctt ccc tct gaa gtt<br>Met Ser Gln Pro Asp Val Pro Leu Ser Gln Leu Leu Pro Ser Glu Val<br>120                        125                  130 | 561 |
| gtt tcc gcg agt gtc cct aag gaa gca ctg gtg atc gtt caa gtg aac<br>Val Ser Ala Ser Val Pro Lys Glu Ala Leu Val Ile Val Gln Val Asn<br>       135                   140                  145 | 609 |
| atg ttt gac tgt ggt gga aca gcc att tgt tcg agt gta tca cat aag<br>Met Phe Asp Cys Gly Gly Thr Ala Ile Cys Ser Ser Val Ser His Lys<br>150                        155                  160 | 657 |
| att gcc gat gca gct aca atg agt acg ttc att cgt agt tgg gca agc<br>Ile Ala Asp Ala Ala Thr Met Ser Thr Phe Ile Arg Ser Trp Ala Ser<br>165                 170                  175                  180 | 705 |
| acc act aaa aca tct cgt agt ggg ggt tca act gct gcc gtt aca gat<br>Thr Thr Lys Thr Ser Arg Ser Gly Gly Ser Thr Ala Ala Val Thr Asp<br>                     185                  190                  195 | 753 |
| cag aaa ttg att cct tct ttc gac tcg gca tct cta ttc cca cct agt<br>Gln Lys Leu Ile Pro Ser Phe Asp Ser Ala Ser Leu Phe Pro Pro Ser<br>200                        205                  210 | 801 |
| gaa cga ttg aca tct cca tca ggg atg tca gag ata cca ttt tcc agt<br>Glu Arg Leu Thr Ser Pro Ser Gly Met Ser Glu Ile Pro Phe Ser Ser<br>                     215                  220                  225 | 849 |
| acc cca gag gat aca gaa gat gat aaa act gtc agc aag aga ttt gtg<br>Thr Pro Glu Asp Thr Glu Asp Asp Lys Thr Val Ser Lys Arg Phe Val<br>230                        235                  240 | 897 |
| ttc gat ttt gca aag ata aca tct gta cgt gaa aag ttg caa gta ttg<br>Phe Asp Phe Ala Lys Ile Thr Ser Val Arg Glu Lys Leu Gln Val Leu<br>245                 250                  255                  260 | 945 |
| atg cat gat aac tac aaa agc cgc agg caa aca agg gtt gag gtg gtt<br>Met His Asp Asn Tyr Lys Ser Arg Arg Gln Thr Arg Val Glu Val Val<br>                     265                  270                  275 | 993 |
| act tct cta ata tgg aag tcc gtg atg aaa tcc act cca gcc ggt ttt<br>Thr Ser Leu Ile Trp Lys Ser Val Met Lys Ser Thr Pro Ala Gly Phe<br>280                        285                  290 | 1041 |
| tta cca gtg gta cat cat gcc gtg aac ctt aga aag aaa atg gac cca<br>Leu Pro Val Val His His Ala Val Asn Leu Arg Lys Lys Met Asp Pro<br>                     295                  300                  305 | 1089 |
| cca tta caa gat gtt tca ttc gga aat cta tct gta act gtt tcg gcg<br>Pro Leu Gln Asp Val Ser Phe Gly Asn Leu Ser Val Thr Val Ser Ala<br>310                        315                  320 | 1137 |
| ttc tta cca gca aca aca acg aca aca aca aat gcg gtc aac aag aca<br>Phe Leu Pro Ala Thr Thr Thr Thr Thr Thr Asn Ala Val Asn Lys Thr<br>325                 330                  335                  340 | 1185 |
| atc aat agt acg agt agt gaa tca caa gtg gta ctt cat gag tta cat<br>Ile Asn Ser Thr Ser Ser Glu Ser Gln Val Val Leu His Glu Leu His<br>                     345                  350                  355 | 1233 |
| gat ttt ata gct cag atg agg agt gaa ata gat aag gtc aag ggt gat<br>Asp Phe Ile Ala Gln Met Arg Ser Glu Ile Asp Lys Val Lys Gly Asp<br>360                        365                  370 | 1281 |
| aaa ggt agc ttg gag aaa gtc att caa aat ttt gct tct ggt cat gat<br>Lys Gly Ser Leu Glu Lys Val Ile Gln Asn Phe Ala Ser Gly His Asp<br>                     375                  380                  385 | 1329 |
| gct tca ata aag aaa atc aat gat gtt gaa gtg ata aac ttt tgg ata<br>Ala Ser Ile Lys Lys Ile Asn Asp Val Glu Val Ile Asn Phe Trp Ile<br>390                        395                  400 | 1377 |
| agt agc tgg tgc agg atg gga tta tac gag att gat ttt ggt tgg gga<br>Ser Ser Trp Cys Arg Met Gly Leu Tyr Glu Ile Asp Phe Gly Trp Gly<br>405                 410                  415                  420 | 1425 |
| aag cca att tgg gta aca gtt gat cca aat atc aag ccg aac aag aat<br>Lys Pro Ile Trp Val Thr Val Asp Pro Asn Ile Lys Pro Asn Lys Asn<br>                     425                  430                  435 | 1473 |

```
tgt ttt ttc atg aat gat acg aaa tgt ggt gaa gga ata gaa gtt tgg      1521
Cys Phe Phe Met Asn Asp Thr Lys Cys Gly Glu Gly Ile Glu Val Trp
            440                 445                 450 gcg agc ttt ctt gag gat gat atg gct aag ttc gag ctt cac cta agt      1569
Ala Ser Phe Leu Glu Asp Asp Met Ala Lys Phe Glu Leu His Leu Ser
            455                 460                 465 gaa atc ctt gaa ttg att tgatattgca ttatctacat gtgttccgta             1617
Glu Ile Leu Glu Leu Ile
        470 atcatgattt tctccatttc cctttccgta gttggttaca agaaccaaa taaaggaaaa     1677 gaaaaaactt gtactgctcg atgctttgac attttccatg ttcatccgta aattcccatc    1737 agaaaagagt ttcaaatatt agggtattaa aaaaaaaaaa aaaaaaaa                 1785

<210> SEQ ID NO 14
<211> LENGTH: 474
<212> TYPE: PRT
<213> ORGANISM: Papaver somniferum

<400> SEQUENCE: 14
```

Met Ala Thr Met Tyr Ser Ala Ala Val Glu Val Ile Ser Lys Glu Thr
 1               5                  10                  15

Ile Lys Pro Thr Thr Pro Thr Pro Ser Gln Leu Lys Asn Phe Asn Leu
                20                  25                  30

Ser Leu Leu Asp Gln Cys Phe Pro Leu Tyr Tyr Val Pro Ile Ile
            35                  40                  45

Leu Phe Tyr Pro Ala Thr Ala Ala Asn Ser Thr Gly Ser Ser Asn His
        50                  55                  60

His Asp Asp Leu Asp Leu Leu Lys Ser Ser Leu Ser Lys Thr Leu Val
 65                 70                  75                  80

His Phe Tyr Pro Met Ala Gly Arg Met Ile Asp Asn Ile Leu Val Asp
                85                  90                  95

Cys His Asp Gln Gly Ile Asn Phe Tyr Lys Val Lys Ile Arg Gly Lys
            100                 105                 110

Met Cys Glu Phe Met Ser Gln Pro Asp Val Pro Leu Ser Gln Leu Leu
        115                 120                 125

Pro Ser Glu Val Val Ser Ala Ser Val Pro Lys Glu Ala Leu Val Ile
    130                 135                 140

Val Gln Val Asn Met Phe Asp Cys Gly Gly Thr Ala Ile Cys Ser Ser
145                 150                 155                 160

Val Ser His Lys Ile Ala Asp Ala Ala Thr Met Ser Thr Phe Ile Arg
                165                 170                 175

Ser Trp Ala Ser Thr Thr Lys Thr Ser Arg Ser Gly Gly Ser Thr Ala
            180                 185                 190

Ala Val Thr Asp Gln Lys Leu Ile Pro Ser Phe Asp Ser Ala Ser Leu
        195                 200                 205

Phe Pro Pro Ser Glu Arg Leu Thr Ser Pro Ser Gly Met Ser Glu Ile
    210                 215                 220

Pro Phe Ser Ser Thr Pro Glu Asp Thr Glu Asp Asp Lys Thr Val Ser
225                 230                 235                 240

Lys Arg Phe Val Phe Asp Phe Ala Lys Ile Thr Ser Val Arg Glu Lys
                245                 250                 255

Leu Gln Val Leu Met His Asp Asn Tyr Lys Ser Arg Arg Gln Thr Arg
            260                 265                 270

Val Glu Val Val Thr Ser Leu Ile Trp Lys Ser Val Met Lys Ser Thr
        275                 280                 285

```
Pro Ala Gly Phe Leu Pro Val His His Ala Val Asn Leu Arg Lys
    290                 295                 300

Lys Met Asp Pro Pro Leu Gln Asp Val Ser Phe Gly Asn Leu Ser Val
305                 310                 315                 320

Thr Val Ser Ala Phe Leu Pro Ala Thr Thr Thr Thr Thr Asn Ala
                325                 330                 335

Val Asn Lys Thr Ile Asn Ser Thr Ser Ser Glu Ser Gln Val Val Leu
            340                 345                 350

His Glu Leu His Asp Phe Ile Ala Gln Met Arg Ser Glu Ile Asp Lys
                355                 360                 365

Val Lys Gly Asp Lys Gly Ser Leu Glu Lys Val Ile Gln Asn Phe Ala
    370                 375                 380

Ser Gly His Asp Ala Ser Ile Lys Lys Ile Asn Asp Val Glu Val Ile
385                 390                 395                 400

Asn Phe Trp Ile Ser Ser Trp Cys Arg Met Gly Leu Tyr Glu Ile Asp
                405                 410                 415

Phe Gly Trp Gly Lys Pro Ile Trp Val Thr Val Asp Pro Asn Ile Lys
                420                 425                 430

Pro Asn Lys Asn Cys Phe Phe Met Asn Asp Thr Lys Cys Gly Glu Gly
            435                 440                 445

Ile Glu Val Trp Ala Ser Phe Leu Glu Asp Asp Met Ala Lys Phe Glu
450                 455                 460

Leu His Leu Ser Glu Ile Leu Glu Leu Ile
465                 470
```

<210> SEQ ID NO 15
<211> LENGTH: 1425
<212> TYPE: DNA
<213> ORGANISM: Papaver somniferum
<220> FEATURE:
<221> NAME/KEY: CDS
<222> LOCATION: (1)..(1422)

<400> SEQUENCE: 15

```
atg gca aca atg tat agt gct gct gtt gaa gtg atc tct aag gaa acc      48
Met Ala Thr Met Tyr Ser Ala Ala Val Glu Val Ile Ser Lys Glu Thr
 1               5                  10                  15 att aaa ccc aca act cca acc cca tct caa ctt aaa aac ttc aat ctg      96
Ile Lys Pro Thr Thr Pro Thr Pro Ser Gln Leu Lys Asn Phe Asn Leu
             20                  25                  30 tca ctt ctc gat caa tgt ttt cct tta tat tat tat gtt cca atc att     144
Ser Leu Leu Asp Gln Cys Phe Pro Leu Tyr Tyr Tyr Val Pro Ile Ile
         35                  40                  45 ctt ttc tac cca gcc acc gcc gct aat agt acc ggt agc agt aac cat     192
Leu Phe Tyr Pro Ala Thr Ala Ala Asn Ser Thr Gly Ser Ser Asn His
     50                  55                  60 cat gat gat ctt gac ttg ctt aag agt tct ctt tcc aaa aca cta gtt     240
His Asp Asp Leu Asp Leu Leu Lys Ser Ser Leu Ser Lys Thr Leu Val
 65                  70                  75                  80 cac ttt tat cca atg gct ggt agg atg ata gac aat att ctg gtc gac     288
His Phe Tyr Pro Met Ala Gly Arg Met Ile Asp Asn Ile Leu Val Asp
                 85                  90                  95 tgt cat gac caa ggg att aac ttt tac aaa gtt aaa att aga ggt aaa     336
Cys His Asp Gln Gly Ile Asn Phe Tyr Lys Val Lys Ile Arg Gly Lys
            100                 105                 110 atg tgt gag ttc atg tcg caa ccg gat gtg cca cta agc cag ctt ctt     384
Met Cys Glu Phe Met Ser Gln Pro Asp Val Pro Leu Ser Gln Leu Leu
        115                 120                 125
```

| | | |
|---|---|---|
| ccc tct gaa gtt gtt tcc gcg agt gtc cct aag gaa gca ctg gtg atc<br>Pro Ser Glu Val Val Ser Ala Ser Val Pro Lys Glu Ala Leu Val Ile<br>130                            135                         140 | | 432 |
| gtt caa gtg aac atg ttt gac tgt ggt gga aca gcc att tgt tcg agt<br>Val Gln Val Asn Met Phe Asp Cys Gly Gly Thr Ala Ile Cys Ser Ser<br>145                            150                         155                 160 | | 480 |
| gta tca cat aag att gcc gat gca gct aca atg agt acg ttc att cgt<br>Val Ser His Lys Ile Ala Asp Ala Ala Thr Met Ser Thr Phe Ile Arg<br>                          165                         170                         175 | | 528 |
| agt tgg gca agc acc act aaa aca tct cgt agt ggg ggt tca act gct<br>Ser Trp Ala Ser Thr Thr Lys Thr Ser Arg Ser Gly Gly Ser Thr Ala<br>                  180                         185                         190 | | 576 |
| gcc gtt aca gat cag aaa ttg att cct tct ttc gac tcg gca tct cta<br>Ala Val Thr Asp Gln Lys Leu Ile Pro Ser Phe Asp Ser Ala Ser Leu<br>              195                         200                         205 | | 624 |
| ttc cca cct agt gaa cga ttg aca tct cca tca ggg atg tca gag ata<br>Phe Pro Pro Ser Glu Arg Leu Thr Ser Pro Ser Gly Met Ser Glu Ile<br>210                            215                         220 | | 672 |
| cca ttt tcc agt acc cca gag gat aca gaa gat gat aaa act gtc agc<br>Pro Phe Ser Ser Thr Pro Glu Asp Thr Glu Asp Asp Lys Thr Val Ser<br>225                          230                         235                 240 | | 720 |
| aag aga ttt gtg ttc gat ttt gca aag ata aca tct gta cgt gaa aag<br>Lys Arg Phe Val Phe Asp Phe Ala Lys Ile Thr Ser Val Arg Glu Lys<br>                          245                         250                         255 | | 768 |
| ttg caa gta ttg atg cat gat aac tac aaa agc cgc agg caa aca agg<br>Leu Gln Val Leu Met His Asp Asn Tyr Lys Ser Arg Arg Gln Thr Arg<br>                  260                         265                         270 | | 816 |
| gtt gag gtg gtt act tct cta ata tgg aag tcc gtg atg aaa tcc act<br>Val Glu Val Val Thr Ser Leu Ile Trp Lys Ser Val Met Lys Ser Thr<br>              275                         280                         285 | | 864 |
| cca gcc ggt ttt tta cca gtg gta cat cat gcc gtg aac ctt aga aag<br>Pro Ala Gly Phe Leu Pro Val Val His His Ala Val Asn Leu Arg Lys<br>290                            295                         300 | | 912 |
| aaa atg gac cca cca tta caa gat gtt tca ttc gga aat cta tct gta<br>Lys Met Asp Pro Pro Leu Gln Asp Val Ser Phe Gly Asn Leu Ser Val<br>305                            310                         315                 320 | | 960 |
| act gtt tcg gcg ttc tta cca gca aca aca acg aca aca aca aat gcg<br>Thr Val Ser Ala Phe Leu Pro Ala Thr Thr Thr Thr Thr Thr Asn Ala<br>                          325                         330                         335 | | 1008 |
| gtc aac aag aca atc aat agt acg agt agt gaa tca caa gtg gta ctt<br>Val Asn Lys Thr Ile Asn Ser Thr Ser Ser Glu Ser Gln Val Val Leu<br>                  340                         345                         350 | | 1056 |
| cat gag tta cat gat ttt ata gct cag atg agg agt gaa ata gat aag<br>His Glu Leu His Asp Phe Ile Ala Gln Met Arg Ser Glu Ile Asp Lys<br>              355                         360                         365 | | 1104 |
| gtc aag ggt gat aaa ggt agc ttg gag aaa gtc att caa aat ttt gct<br>Val Lys Gly Asp Lys Gly Ser Leu Glu Lys Val Ile Gln Asn Phe Ala<br>370                            375                         380 | | 1152 |
| tct ggt cat gat gct tca ata aag aaa atc aat gat gtt gaa gtg ata<br>Ser Gly His Asp Ala Ser Ile Lys Lys Ile Asn Asp Val Glu Val Ile<br>385                            390                         395                 400 | | 1200 |
| aac ttt tgg ata agt agc tgg tgc agg atg gga tta tac gag att gat<br>Asn Phe Trp Ile Ser Ser Trp Cys Arg Met Gly Leu Tyr Glu Ile Asp<br>                          405                         410                         415 | | 1248 |
| ttt ggt tgg gga aag cca att tgg gta aca gtt gat cca aat atc aag<br>Phe Gly Trp Gly Lys Pro Ile Trp Val Thr Val Asp Pro Asn Ile Lys<br>                  420                         425                         430 | | 1296 |
| ccg aac aag aat tgt ttt ttc atg aat gat acg aaa tgt ggt gaa gga<br>Pro Asn Lys Asn Cys Phe Phe Met Asn Asp Thr Lys Cys Gly Glu Gly<br>              435                         440                         445 | | 1344 |

```
ata gaa gtt tgg gcg agc ttt ctt gag gat gat atg gct aag ttc gag    1392
Ile Glu Val Trp Ala Ser Phe Leu Glu Asp Asp Met Ala Lys Phe Glu
    450                 455                 460 ctt cac cta agt gaa atc ctt gaa ttg att tga                        1425
Leu His Leu Ser Glu Ile Leu Glu Leu Ile
465             470

<210> SEQ ID NO 16
<211> LENGTH: 474
<212> TYPE: PRT
<213> ORGANISM: Papaver somniferum

<400> SEQUENCE: 16

Met Ala Thr Met Tyr Ser Ala Ala Val Glu Val Ile Ser Lys Glu Thr
1               5                   10                  15

Ile Lys Pro Thr Thr Pro Thr Pro Ser Gln Leu Lys Asn Phe Asn Leu
            20                  25                  30

Ser Leu Leu Asp Gln Cys Phe Pro Leu Tyr Tyr Val Pro Ile Ile
        35                  40                  45

Leu Phe Tyr Pro Ala Thr Ala Ala Asn Ser Thr Gly Ser Ser Asn His
    50                  55                  60

His Asp Asp Leu Asp Leu Leu Lys Ser Ser Leu Ser Lys Thr Leu Val
65                  70                  75                  80

His Phe Tyr Pro Met Ala Gly Arg Met Ile Asp Asn Ile Leu Val Asp
                85                  90                  95

Cys His Asp Gln Gly Ile Asn Phe Tyr Lys Val Lys Ile Arg Gly Lys
            100                 105                 110

Met Cys Glu Phe Met Ser Gln Pro Asp Val Pro Leu Ser Gln Leu Leu
        115                 120                 125

Pro Ser Glu Val Val Ser Ala Ser Val Pro Lys Glu Ala Leu Val Ile
    130                 135                 140

Val Gln Val Asn Met Phe Asp Cys Gly Gly Thr Ala Ile Cys Ser Ser
145                 150                 155                 160

Val Ser His Lys Ile Ala Asp Ala Ala Thr Met Ser Thr Phe Ile Arg
                165                 170                 175

Ser Trp Ala Ser Thr Thr Lys Thr Ser Arg Ser Gly Gly Ser Thr Ala
            180                 185                 190

Ala Val Thr Asp Gln Lys Leu Ile Pro Ser Phe Asp Ser Ala Ser Leu
        195                 200                 205

Phe Pro Pro Ser Glu Arg Leu Thr Ser Pro Ser Gly Met Ser Glu Ile
    210                 215                 220

Pro Phe Ser Ser Thr Pro Glu Asp Thr Glu Asp Lys Thr Val Ser
225                 230                 235                 240

Lys Arg Phe Val Phe Asp Phe Ala Lys Ile Thr Ser Val Arg Glu Lys
                245                 250                 255

Leu Gln Val Leu Met His Asp Asn Tyr Lys Ser Arg Arg Gln Thr Arg
            260                 265                 270

Val Glu Val Val Thr Ser Leu Ile Trp Lys Ser Val Met Lys Ser Thr
        275                 280                 285

Pro Ala Gly Phe Leu Pro Val Val His Ala Val Asn Leu Arg Lys
    290                 295                 300

Lys Met Asp Pro Pro Leu Gln Asp Val Ser Phe Gly Asn Leu Ser Val
305                 310                 315                 320

Thr Val Ser Ala Phe Leu Pro Ala Thr Thr Thr Thr Thr Asn Ala
                325                 330                 335
```

```
Val Asn Lys Thr Ile Asn Ser Thr Ser Ser Glu Ser Gln Val Val Leu
                340                 345                 350

His Glu Leu His Asp Phe Ile Ala Gln Met Arg Ser Glu Ile Asp Lys
        355                 360                 365

Val Lys Gly Asp Lys Gly Ser Leu Glu Lys Val Ile Gln Asn Phe Ala
    370                 375                 380

Ser Gly His Asp Ala Ser Ile Lys Lys Ile Asn Asp Val Glu Val Ile
385                 390                 395                 400

Asn Phe Trp Ile Ser Ser Trp Cys Arg Met Gly Leu Tyr Glu Ile Asp
                405                 410                 415

Phe Gly Trp Gly Lys Pro Ile Trp Val Thr Val Asp Pro Asn Ile Lys
            420                 425                 430

Pro Asn Lys Asn Cys Phe Phe Met Asn Asp Thr Lys Cys Gly Glu Gly
        435                 440                 445

Ile Glu Val Trp Ala Ser Phe Leu Glu Asp Asp Met Ala Lys Phe Glu
    450                 455                 460

Leu His Leu Ser Glu Ile Leu Glu Leu Ile
465                 470

<210> SEQ ID NO 17
<211> LENGTH: 1514
<212> TYPE: DNA
<213> ORGANISM: Papaver somniferum

<400> SEQUENCE: 17
ccattatcaa tcctgttaaa cagttaaaca ctttggatat atggcaacaa tgtatagtgc      60
tgctgttgaa gtgatctcta aggaaaccat taaacccaca actccaaccc catctcaact     120
taaaaacttc aatctgtcac ttctcgatca atgttttcct ttatattatt atgttccaat     180
cattcttttc tacccagcca ccgccgctaa tagtaccggt agcagtaacc atcatgatga     240
tcttgacttg cttaagagtt ctcttttcca aacactagtt cacttttatc caatggctgg     300
taggatgata gacaatattc tggtcgactg tcatgaccaa ggattaact tttacaaagt      360 taaaattaga ggtaaaatgt gtgacttcat gtcgcaaccg gatgtgccac taagccagct     420
tcttccctct gaaattgttt ccgcgagtgt ccctaaggaa gcactggtga tcgttcaagt     480
gaacatgttt gactgtggtg aacagccat tgttcgagt gtatcacata agattgcgga      540
tgcagctaca atgagtacgt tcattcgtag ttgggcaagc accactaaaa catctcgtag     600
tgggggtgca actgctgccg ttacagatca gaaattgatt ccttctttcg actcggcatc     660
tctattccca cctagtgaac gattgacatc tccatcaggg atgtcagaga taccattttc     720
cagtacccca gaggatacag aagatgataa aactgtcagc aagagatctg tgttcgattt     780
tgcaaagata acatctgtac gtgaaaagtt gcaagtattg atgcatgata actacaaaag     840
ccgcaggcca acaagggttg aggtggttac ttctctaata tggaagtccg tgatgaaatc     900
cactccagcc ggttttttac cagtggtaca tcatgccgtg aaccttagaa agaaaatgga     960
cccaccatta caagatgttt cattcggaaa tctatctgta actgtttcgg cgttcttacc    1020
agcaacaaca acgacaacaa caaatgcggt caacaagaca atcaatagta cgagtagtga    1080
atcacaagtg gtacttcatg agttacatga ttttatagct cagatgagga gtgaaataga    1140
taaggtcaag ggtgataaag gtagcttgga gaaagtcatt caaaatttg cttctggtca     1200 tgatgcttca ataagaaaaa tcaatgatgt tgaagtgata aacttttgga taagtagctg    1260
gtgcaggatg ggattatacg agattgattt tggttgggga aagccaattt gggtaacagt    1320
```

-continued

```
tgatccaaat atcaagccga acaagaattg ttttttcatg aatgatacga aatgtggtga   1380
aggaatagaa gtttgggcga gctttcttga ggatgatatg gctaagttcg agcttcacct   1440
aagtgaaatc cttgaattga tttgatattg cattatctac atgtgttccg taatcatgat   1500
tttctccatt tccc                                                     1514

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Avr II
      primer

<400> SEQUENCE: 18
ccctagggga aatggagaaa atcatgatta cggaacac                             38

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Xho I
      primer

<400> SEQUENCE: 19
cctcgagcca ttatcaatcc tgttaaacag ttaaacac                             38
```